United States Patent
Fan et al.

(10) Patent No.: US 12,257,335 B2
(45) Date of Patent: Mar. 25, 2025

(54) PERSONAL CARE COMPOSITIONS

(71) Applicant: Colgate-Palmolive Company, New York, NY (US)

(72) Inventors: Aixing Fan, Bridgewater, NJ (US); Thomas Boyd, Metuchen, NJ (US); Lan Le, Pennsauken, NJ (US)

(73) Assignee: Colgate-Palmolive Company, New York, NY (US)

( * ) Notice: Subject to any disclaimer, the term of this patent is extended or adjusted under 35 U.S.C. 154(b) by 615 days.

(21) Appl. No.: 17/309,540

(22) PCT Filed: Dec. 6, 2018

(86) PCT No.: PCT/US2018/064190
§ 371 (c)(1),
(2) Date: Jun. 4, 2021

(87) PCT Pub. No.: WO2020/117239
PCT Pub. Date: Jun. 11, 2020

(65) Prior Publication Data
US 2022/0000755 A1 Jan. 6, 2022

(51) Int. Cl.
*A61K 8/81* (2006.01)
*A61Q 17/00* (2006.01)
*A61Q 19/00* (2006.01)

(52) U.S. Cl.
CPC .......... *A61K 8/8182* (2013.01); *A61K 8/8147* (2013.01); *A61Q 17/00* (2013.01); *A61Q 19/007* (2013.01)

(58) Field of Classification Search
CPC .... A61K 8/8182; A61K 8/8147; A61Q 17/00; A61Q 19/007
See application file for complete search history.

(56) References Cited

U.S. PATENT DOCUMENTS

| | | | |
|---|---|---|---|
| 4,983,526 A | 1/1991 | Kenhachi et al. | |
| 5,261,426 A | 11/1993 | Kellett et al. | |
| 9,855,448 B2 | 1/2018 | Fares et al. | |
| 2009/0068255 A1 | 3/2009 | Zhi et al. | |
| 2012/0219515 A1* | 8/2012 | Barrett | A61K 8/817 424/59 |
| 2021/0032496 A1 | 2/2021 | Yonezawa et al. | |

FOREIGN PATENT DOCUMENTS

| | | | |
|---|---|---|---|
| CN | 102429835 | | 5/2012 |
| CN | 111989375 | | 11/2020 |
| DE | 3147024 | | 6/1983 |
| FR | 2836633 | | 9/2003 |
| WO | 1986/005391 | | 9/1986 |
| WO | WO198605391 | * | 9/1986 |
| WO | 2011/017491 | | 2/2011 |
| WO | 2018/215136 | | 11/2018 |

OTHER PUBLICATIONS

Eeman et al., 2018, "Polymeric Barrier Films to Protect Skin from Air Pollutants", IFSCC magazine retrieved from the Internet www.ifscc.org.
International Search Report and the Written Opinion of the International Searching Authority issued in International Application PCT/US2018/064190 mailed Oct. 10, 2019.
Knopp, M.M. et al., "Influence of Copolymer Composition on In Vitro and In Vivo Performance of Celecoxib-PVP/VA Amorphous Solid Dispersions," The AAPS Journal, vol. 18, No. 2, (Jan. 14, 2016), pp. 416-423.
Rask, M.B. et al., "Influence of PVP/VA copolymer composition on drug-polymer solubility," European Journal of Pharmaceutical Sciences, vol. 85 (Jan. 28, 2016) pp. 10-17.
Shigabieva, 2014, "Colloidal-chemical properties of foaming and gel compositions with biologically active components: dissertation," Candidate of Chemical Sciences: 02.00.11.—Kazan, 2014.—158 p., pp. 8, 10, 113, chapter 1.3.
Sutyagin et al. 2003, Chemistry and Physics of Polymers: Textbook.—Tomsk: TPU Publishing House, 2003.—208 p., pp. 132, 140, 142, 151, 173.
Qiu, 2000, "A Guide to the Chemistry and Process Technology of Cosmetic Products," China Light Industry Press, p. 281.

* cited by examiner

Primary Examiner — Jianfeng Song

(57) ABSTRACT

Described herein are personal care compositions comprising a solid vinylpyrrolidone/vinyl acetate copolymer; a vinylpyrrolidone/vinyl acetate copolymer; and a cosmetically acceptable carrier. Methods of making and using the same are also described.

6 Claims, No Drawings

PERSONAL CARE COMPOSITIONS

BACKGROUND

More people die or develop a serious disease from air pollution than from any other environmental factors. Air pollution is linked to about 7 million premature deaths. Outdoor air pollution is associated with ischemic heart disease, stroke, chronic obstructive pulmonary disease, lung cancer, and acute lower respiratory infections in children. Indoor air pollution is linked to stroke, coronary artery disease, ischemic heart disease, chronic obstructive pulmonary disease, acute lower respiratory infections in children, and lung cancer.

Among pollutants that are of concern are criteria air pollutants. Criteria air pollutants are six common air pollutants that include ozone, carbon dioxide, nitrogen oxides, sulfur dioxide, particulate matter, and lead.

Many environmental pollutants are oxidants or catalyze the production of reactive oxygen species (ROS) directly or indirectly. ROS are believed to activate cytoproliferative and/or cell survival signaling mechanisms, including mechanisms that can alter apoptotic and other regulated pathways that may be involved in the pathogenesis of a number of skin disorders, including photosensitivity diseases and some types of cutaneous malignancy.

The skin possesses an array of defense mechanisms that interact with toxicants to obviate their deleterious effects. These protective mechanisms include non-enzymatic and enzymatic molecules that function as potent antioxidants or oxidant-degrading systems. Unfortunately, these homeostatic defenses, although highly effective, have limited capacity and can be overwhelmed, thereby leading to increased ROS in the skin that can foster the development of dermatological diseases.

Although many advances in the art of formulating lotions have been made, many more challenges remain.

BRIEF SUMMARY

Some embodiments of the present invention are directed to a topical composition that comprises a combination of ingredients that block the effects of gaseous pollutants to a patient's skin. Specifically, the present invention is related to a topical composition for use in reducing exposure of gaseous pollutants to the skin, prepared by mixing sequentially into a skin lotion (a) solid vinylpyrrolidone/vinyl acetate copolymer, and (b) vinylpyrrolidone/vinyl acetate copolymer dissolved in a solvent.

One of the advantages of the present invention is that the topical composition prepared by mixing sequentially into a skin lotion (a) solid vinylpyrrolidone/vinyl acetate copolymer, and (b) vinylpyrrolidone/vinyl acetate copolymer dissolved in a solvent, exhibit a synergistic effect of lowering the exposure of ozone transmission through the topical composition.

The vinylpyrrolidone/vinyl acetate copolymer is a linear, random copolymer produced by the free-radical polymerization of vinylpyrrolidone monomers and vinyl acetate monomers in a particular ratio.

The solid vinylpyrrolidone/vinyl acetate copolymer may be a powder, microspheres, flakes, or pellets. Under one embodiment the solid vinylpyrrolidone/vinyl acetate copolymer is a powder.

The vinylpyrrolidone/vinyl acetate copolymer dissolved in a solvent may be dissolved in a weight ratio range of about 40 wt % to about 60 wt %. Under one embodiment, the vinylpyrrolidone/vinyl acetate copolymer is dissolved in the solvent at about 50 wt %.

The molecular weight of the vinylpyrrolidone/vinyl acetate copolymer is in the range of about 10,000 g/mol to about 100,000 g/mol.

The topical composition prepared by mixing sequentially into a skin lotion (a) solid vinylpyrrolidone/vinyl acetate copolymer, and (b) vinylpyrrolidone/vinyl acetate copolymer dissolved in a solvent. Under an embodiment, the weight ratio of the copolymer contents of (a) to (b) is about 8:1 to about 0.4:1. Under an embodiment, the weight ratio of the copolymer contents of (a) to (b) is about 8:1 to about 0.5:1. Under an embodiment, the weight ratio of the copolymer contents of (a) to (b) is about 8:1 to about 0.67:1.

Vinylpyrrolidone/vinyl acetate copolymers dissolve in polar solvents. These solvent include solvents that are small organic compounds which contain atoms with lone pairs, such as oxygen, or nitrogen. The solvent should not have a high degree of hydrocarbon-like characteristic. Acceptable solvents include alcohols, esters, ketones, and water.

The balance of the topical composition is any topical composition that is compatible with both vinylpyrrolidone/vinyl acetate copolymers.

The topical composition is prepared by mixing sequentially into a skin lotion (a) solid vinylpyrrolidone/vinyl acetate copolymer, and (b) vinylpyrrolidone/vinyl acetate copolymer dissolved in a solvent. The steps for preparing the topical composition include: preparing base skin lotion, adding to it solid vinylpyrrolidone/vinyl acetate copolymer, and then adding to that vinylpyrrolidone/vinyl acetate copolymer dissolved in a solvent. Alternatively, the steps for preparing the topical composition include: preparing base skin lotion, adding to it vinylpyrrolidone/vinyl acetate copolymer dissolved in a solvent, and then adding to that solid vinylpyrrolidone/vinyl acetate copolymer. The term "sequentially" means that ingredients (a) and (b) are not added at the same time, but one after each other, in any suitable order.

It has been observed that the addition of solid vinylpyrrolidone/vinyl acetate copolymer at 1.0 wt % in a lotion exhibits ozone blocking at about 11%. It has also been observed that the addition of vinylpyrrolidone/vinyl acetate copolymer dissolved in pure ethanol at 1.0 wt % in a lotion exhibits ozone blocking at about 10%. However, the addition of both solid vinylpyrrolidone/vinyl acetate copolymer and dissolved vinylpyrrolidone/vinyl acetate copolymer, each at 1 wt % level in a lotion, exhibits ozone blocking at about 32%. This is an unusual and unexpected large increase in the ozone blocking ability of the lotion that comprises the solid and dissolved vinylpyrrolidone/vinyl acetate copolymer. This substantial increase is repeatable, and is statistically significant.

The present invention is also directed to a method for reducing exposure of gaseous pollutants to skin of a patient for skin, comprising applying to an area of skin the topical composition prepared by mixing sequentially into a skin lotion (a) solid vinylpyrrolidone/vinyl acetate copolymer, and (b) vinylpyrrolidone/vinyl acetate copolymer dissolved in a solvent.

The method comprises the steps of placing the topical composition onto a small portion of a patient's skin, and spreading the topical composition onto a larger section of the patient's skin to form a layer of the topical composition; or the steps of placing the topical composition onto a patient's hand, and spreading the topical composition onto a larger section of the patient's skin to form a layer of the topical composition; or the steps of placing the topical composition onto a device, and spreading the topical composition onto a larger section of the patient's skin to form a layer of the topical composition.

The invention is defined by at least thirty-two aspects.

In the first aspect, the invention relates to a topical composition for use in reducing exposure of gaseous pollutants to the skin, prepared by mixing sequentially into a skin lotion (a) solid vinylpyrrolidone/vinyl acetate copolymer, and (b) vinylpyrrolidone/vinyl acetate copolymer dissolved in a solvent.

In the second aspect, the invention relates to a topical composition for use in reducing exposure of gaseous pollutants to skin, prepared by mixing sequentially into a skin lotion (a) solid vinylpyrrolidone/vinyl acetate copolymer, and (b) vinylpyrrolidone/vinyl acetate copolymer dissolved in a solvent, wherein the weight ratio of the copolymer content of (a) to (b) is about 8:1 to about 0.4:1.

In the third aspect, the invention relates to a topical composition for use in reducing exposure of gaseous pollutants to skin, prepared by mixing sequentially into a skin lotion (a) solid vinylpyrrolidone/vinyl acetate copolymer, and (b) vinylpyrrolidone/vinyl acetate copolymer dissolved in a solvent, wherein the weight ratio of the copolymer content of (a) to (b) is about 6:1 to about 0.67:1.

In the fourth aspect, the invention relates to a topical composition for use in reducing exposure of gaseous pollutants to skin, prepared by mixing sequentially into a skin lotion (a) solid vinylpyrrolidone/vinyl acetate copolymer, and (b) vinylpyrrolidone/vinyl acetate copolymer dissolved in a solvent, wherein the weight ratio of the copolymer content of (a) to (b) is about 3:1 to about 1:1.

In the fifth aspect, the invention relates to a topical composition for use in reducing exposure of gaseous pollutants to skin, prepared by mixing sequentially into a skin lotion (a) solid vinylpyrrolidone/vinyl acetate copolymer, and (b) vinylpyrrolidone/vinyl acetate copolymer dissolved in a solvent, wherein the solid vinylpyrrolidone/vinyl acetate copolymer has a molecular weight in the range of about 10,000 g/mol to about 100,000 g/mol.

In the sixth aspect, the invention relates to a topical composition for use in reducing exposure of gaseous pollutants to skin, prepared by mixing sequentially into a skin lotion (a) solid vinylpyrrolidone/vinyl acetate copolymer, and (b) vinylpyrrolidone/vinyl acetate copolymer dissolved in a solvent, wherein the solid vinylpyrrolidone/vinyl acetate copolymer has a molecular weight in the range of about 30,000 g/mol to about 70,000 g/mol.

In the seventh aspect, the invention relates to a topical composition for use in reducing exposure of gaseous pollutants to skin, prepared by mixing sequentially into a skin lotion (a) solid vinylpyrrolidone/vinyl acetate copolymer, and (b) vinylpyrrolidone/vinyl acetate copolymer dissolved in a solvent, wherein the vinylpyrrolidone/vinyl acetate copolymer dissolved in the solvent has a molecular weight in the range of about 10,000 g/mol to about 100,000 g/mol.

In the eighth aspect, the invention relates to a topical composition for use in reducing exposure of gaseous pollutants to skin, prepared by mixing sequentially into a skin lotion (a) solid vinylpyrrolidone/vinyl acetate copolymer, and (b) vinylpyrrolidone/vinyl acetate copolymer dissolved in a solvent, wherein the vinylpyrrolidone/vinyl acetate copolymer dissolved in the solvent has a molecular weight in the range of about 30,000 g/mol to about 70,000 g/mol.

In the ninth aspect, the invention relates to a topical composition for use in reducing exposure of gaseous pollutants to skin, prepared by mixing sequentially into a skin lotion (a) solid vinylpyrrolidone/vinyl acetate copolymer, and (b) vinylpyrrolidone/vinyl acetate copolymer dissolved in a solvent, wherein the solvent is selected from the group consisting of alcohols, esters, ketones, and mixtures thereof.

In the tenth aspect, the invention relates to a topical composition for use in reducing exposure of gaseous pollutants to skin, prepared by mixing sequentially into a skin lotion (a) solid vinylpyrrolidone/vinyl acetate copolymer, and (b) vinylpyrrolidone/vinyl acetate copolymer dissolved in a solvent, wherein the solvent is selected from the group consisting of ethanol, n-propanol, i-propanol, methyl acetate, ethyl acetate, methyl propionate, ethyl propionate, acetone, methyl ethyl ketone, 3-pentone, and mixtures thereof.

In the eleventh aspect, the invention relates to a topical composition for use in reducing exposure of gaseous pollutants to the skin, prepared by mixing sequentially into a skin lotion (a) solid vinylpyrrolidone/vinyl acetate copolymer, and (b) vinylpyrrolidone/vinyl acetate copolymer dissolved in ethanol.

In the twelfth aspect, the invention relates to a topical composition for use in reducing exposure of gaseous pollutants to skin, prepared by mixing sequentially into a skin lotion (a) solid vinylpyrrolidone/vinyl acetate copolymer, and (b) vinylpyrrolidone/vinyl acetate copolymer dissolved in a solvent, wherein the composition further comprises water, a humectant, a preservative, an exfoliator, a lubricant, an emollient, and an emulsifier.

In the thirteenth aspect, the invention relates to a topical composition for use in reducing exposure of gaseous pollutants to skin, prepared by mixing sequentially into a skin lotion (a) solid vinylpyrrolidone/vinyl acetate copolymer, and (b) vinylpyrrolidone/vinyl acetate copolymer dissolved in a solvent, wherein the composition is a fully formulated topical lotion for use in reducing exposure of gaseous pollutants to skin of a patient.

In the fourteenth aspect, the invention relates to a topical composition for use in reducing exposure of gaseous pollutants to skin, prepared by mixing sequentially into a skin lotion (a) solid vinylpyrrolidone/vinyl acetate copolymer, and (b) vinylpyrrolidone/vinyl acetate copolymer dissolved in a solvent, wherein a 20-micrometer layer of the composition reduces the transmission of ozone by at least 20% compared to the composition without the solid vinylpyrrolidone/vinyl acetate copolymer and the vinylpyrrolidone/vinyl acetate copolymer dissolved in a solvent.

In the fifteenth aspect, the invention relates to a topical composition for use in reducing exposure of gaseous pollutants to skin, prepared by mixing sequentially into a skin lotion (a) solid vinylpyrrolidone/vinyl acetate copolymer, and (b) vinylpyrrolidone/vinyl acetate copolymer dissolved in a solvent, wherein a 20-micrometer layer of the composition reduces the transmission of ozone by at least 20% compared to the composition without the solid vinylpyrrolidone/vinyl acetate copolymer.

In the sixteenth aspect, the invention relates to a topical composition for use in reducing exposure of gaseous pollutants to skin, prepared by mixing sequentially into a skin lotion (a) solid vinylpyrrolidone/vinyl acetate copolymer, and (b) vinylpyrrolidone/vinyl acetate copolymer dissolved in a solvent, wherein a 20-micrometer layer of the composition reduces the transmission of ozone by at least 20% compared to the composition without the vinylpyrrolidone/vinyl acetate copolymer dissolved in a solvent.

In the seventeenth aspect, the invention relates to a method for reducing exposure of gaseous pollutants to skin of a patient for skin, comprising applying to an area of skin the topical composition prepared by mixing sequentially into a skin lotion (a) solid vinylpyrrolidone/vinyl acetate copolymer, and (b) vinylpyrrolidone/vinyl acetate copolymer dissolved in a solvent.

In the eighteenth aspect, the invention relates to a method for reducing exposure of gaseous pollutants to skin of a patient for skin, comprising applying to an area of skin the topical composition prepared by mixing sequentially into a skin lotion (a) solid vinylpyrrolidone/vinyl acetate copolymer, and (b) vinylpyrrolidone/vinyl acetate copolymer dissolved in a solvent, wherein the weight ratio of the copolymer content of (a) to (b) is about 8:1 to about 0.4:1.

In the nineteenth aspect, the invention relates to a method for reducing exposure of gaseous pollutants to skin of a patient for skin, comprising applying to an area of skin the topical composition prepared by mixing sequentially into a skin lotion (a) solid vinylpyrrolidone/vinyl acetate copolymer, and (b) vinylpyrrolidone/vinyl acetate copolymer dissolved in a solvent, wherein the weight ratio of the copolymer content of (a) to (b) is about 6:1 to about 0.67:1.

In the twentieth aspect, the invention relates to a method for reducing exposure of gaseous pollutants to skin of a patient for skin, comprising applying to an area of skin the topical composition prepared by mixing sequentially into a skin lotion (a) solid vinylpyrrolidone/vinyl acetate copolymer, and (b) vinylpyrrolidone/vinyl acetate copolymer dissolved in a solvent, wherein the weight ratio of the copolymer content of (a) to (b) is about 3:1 to about 1:1.

In the twenty-first aspect, the invention relates to a method for reducing exposure of gaseous pollutants to skin of a patient for skin, comprising applying to an area of skin the topical composition prepared by mixing sequentially into a skin lotion (a) solid vinylpyrrolidone/vinyl acetate copolymer, and (b) vinylpyrrolidone/vinyl acetate copolymer dissolved in a solvent, wherein the solid vinylpyrrolidone/vinyl acetate copolymer has a molecular weight in the range of about 10,000 g/mol to about 100,000 g/mol.

In the twenty-second aspect, the invention relates to a method for reducing exposure of gaseous pollutants to skin of a patient for skin, comprising applying to an area of skin the topical composition prepared by mixing sequentially into a skin lotion (a) solid vinylpyrrolidone/vinyl acetate copolymer, and (b) vinylpyrrolidone/vinyl acetate copolymer dissolved in a solvent, wherein the solid vinylpyrrolidone/vinyl acetate copolymer has a molecular weight in the range of about 30,000 g/mol to about 70,000 g/mol.

In the twenty-third aspect, the invention relates to a method for reducing exposure of gaseous pollutants to skin of a patient for skin, comprising applying to an area of skin the topical composition prepared by mixing sequentially into a skin lotion (a) solid vinylpyrrolidone/vinyl acetate copolymer, and (b) vinylpyrrolidone/vinyl acetate copolymer dissolved in a solvent, wherein the vinylpyrrolidone/vinyl acetate copolymer dissolved in the solvent has a molecular weight in the range of about 10,000 g/mol to about 100,000 g/mol.

In the twenty-fourth aspect, the invention relates to a method for reducing exposure of gaseous pollutants to skin of a patient for skin, comprising applying to an area of skin the topical composition prepared by mixing sequentially into a skin lotion (a) solid vinylpyrrolidone/vinyl acetate copolymer, and (b) vinylpyrrolidone/vinyl acetate copolymer dissolved in a solvent, wherein the vinylpyrrolidone/vinyl acetate copolymer dissolved in the solvent has a molecular weight in the range of about 30,000 g/mol to about 70,000 g/mol.

In the twenty-fifth aspect, the invention relates to a method for reducing exposure of gaseous pollutants to skin of a patient for skin, comprising applying to an area of skin the topical composition prepared by mixing sequentially into a skin lotion (a) solid vinylpyrrolidone/vinyl acetate copolymer, and (b) vinylpyrrolidone/vinyl acetate copolymer dissolved in a solvent, wherein the solvent is selected from the group consisting of alcohols, esters, ketones, and mixtures thereof.

In the twenty-sixth aspect, the invention relates to a method for reducing exposure of gaseous pollutants to skin of a patient for skin, comprising applying to an area of skin the topical composition prepared by mixing sequentially into a skin lotion (a) solid vinylpyrrolidone/vinyl acetate copolymer, and (b) vinylpyrrolidone/vinyl acetate copolymer dissolved in a solvent, wherein the solvent is selected from the group consisting of ethanol, n-propanol, i-propanol, methyl acetate, ethyl acetate, methyl propionate, ethyl propionate, acetone, methyl ethyl ketone, 3-pentone, and mixtures thereof.

In the twenty-seventh aspect, the invention relates to a method for reducing exposure of gaseous pollutants to skin of a patient for skin, comprising applying to an area of skin the topical composition prepared by mixing sequentially into a skin lotion (a) solid vinylpyrrolidone/vinyl acetate copolymer, and (b) vinylpyrrolidone/vinyl acetate copolymer dissolved in a solvent, wherein the solvent is ethanol.

In the twenty-eighth aspect, the invention relates to a method for reducing exposure of gaseous pollutants to skin of a patient for skin, comprising applying to an area of skin the topical composition prepared by mixing sequentially into a skin lotion (a) solid vinylpyrrolidone/vinyl acetate copolymer, and (b) vinylpyrrolidone/vinyl acetate copolymer dissolved in a solvent, wherein the composition further comprises water, a humectant, a preservative, an exfoliator, a lubricant, an emollient, and an emulsifier.

In the twenty-ninth aspect, the invention relates to a method for reducing exposure of gaseous pollutants to skin of a patient for skin, comprising applying to an area of skin the topical composition prepared by mixing sequentially into a skin lotion (a) solid vinylpyrrolidone/vinyl acetate copolymer, and (b) vinylpyrrolidone/vinyl acetate copolymer dissolved in a solvent, wherein the composition is a fully formulated topical lotion for use in reducing exposure of gaseous pollutants to skin of a patient.

In the thirtieth aspect, the invention relates to a method for reducing exposure of gaseous pollutants to skin of a patient for skin, comprising applying to an area of skin the topical composition prepared by mixing sequentially into a skin lotion (a) solid vinylpyrrolidone/vinyl acetate copolymer, and (b) vinylpyrrolidone/vinyl acetate copolymer dissolved in a solvent, wherein a 20-micrometer layer of the composition reduces the transmission of ozone by at least 20% compared to the composition without the solid vinylpyrrolidone/vinyl acetate copolymer and the vinylpyrrolidone/vinyl acetate copolymer dissolved in a solvent.

In the thirty-first aspect, the invention relates to a method for reducing exposure of gaseous pollutants to skin of a patient for skin, comprising applying to an area of skin the topical composition prepared by mixing sequentially into a skin lotion (a) solid vinylpyrrolidone/vinyl acetate copolymer, and (b) vinylpyrrolidone/vinyl acetate copolymer dissolved in a solvent, wherein a 20-micrometer layer of the composition reduces the transmission of ozone by at least 20% compared to the composition without the solid vinylpyrrolidone/vinyl acetate copolymer.

In the thirty-second aspect, the invention relates to a method for reducing exposure of gaseous pollutants to skin of a patient for skin, comprising applying to an area of skin the topical composition prepared by mixing sequentially into a skin lotion (a) solid vinylpyrrolidone/vinyl acetate copolymer, and (b) vinylpyrrolidone/vinyl acetate copolymer dissolved in a solvent, wherein a 20-micrometer layer of the composition reduces the transmission of ozone by at least 20% compared to the composition without the vinylpyrrolidone/vinyl acetate copolymer dissolved in a solvent.

DETAILED DESCRIPTION

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation. Further, although certain methods are described with reference to certain steps that are presented herein in certain order, in many instances, these steps may be performed in any order as may be appreciated by one skilled in the art, and the methods are not limited to the particular arrangement of steps disclosed herein.

As used herein and in the appended claims, the singular forms "a", "an", and "the" include plural references unless the context clearly dictates otherwise. The singular form of any class of the ingredients refers not only to one chemical species within that class, but also to a mixture of those chemical species; for example, the term "polymer" in the singular form, may refer to a mixture of compounds each of which is also a polymer. The terms "a" (or "an"), "one or more" and "at least one" may be used interchangeably herein. The terms "comprising", "including", and "having" may be used interchangeably.

When referring to a member of a Markush group, wherein the member is in a plural form, then the reference is made to any species of that member. For example, the phrase "the solvent is selected from the group consisting of alcohols, . . . " means that the solvent can be a single alcohol (such as ethanol), or a mixture of alcohols.

The abbreviations and symbols as used herein, unless indicated otherwise, take their ordinary meaning. The term "wt %" means percent by weight. The symbol "ppb" means parts per billion. The unit "g/mol" means grams per mole, the unit "mg" means milligrams. The characters "α", "ρ", and "γ" are Greek letters alpha, beta, and gamma, respectively.

The symbols "—", "=", superscripted "—" in a chemical formula mean a single bond, a double bond, a negative charge, respectively; the symbols "-" and "=" in mathematical context mean minus and equals, respectively. When referring to chemical structures, and names, symbols "H", "C", and "O", are chemical symbols for hydrogen, carbon, and oxygen, respectively.

Brackets around a species, such as "[$O_3$]", indicate the concentration of the species recited in the bracket. The concentration may be express in mol/L or in ppb.

The term "about" when referring to a number means ±10% Mo. For example, the phrase "about 30,000" refers to a number between and including 27,000 and 33,000.

As used throughout, ranges are used as shorthand for describing each and every value that is within the range. Any value within the range can be selected as the terminus of the range.

The term "polymer", as for example in the phrase "acrylic acid polymer", is to be interpreted broadly. Examples of polymers include both a homopolymer (a polymer comprising a single species of monomer) and a copolymer. The term "copolymer" means a polymer comprising more than one species of monomer. The copolymer of the present invention consists of, or comprises essentially of, one or more linear chain copolymers.

In some embodiments, the present invention is directed to a topical composition that comprises a combination of ingredients that block the effects of gaseous pollutants to a patient's skin.

In other embodiments, the present invention is related to a topical composition for use in reducing exposure of gaseous pollutants to skin, prepared by mixing sequentially into a skin lotion (a) solid vinylpyrrolidone/vinyl acetate copolymer, and (b) vinylpyrrolidone/vinyl acetate copolymer dissolved in a solvent.

One of the advantages of the present invention is that the topical composition prepared by mixing sequentially into a skin lotion (a) solid vinylpyrrolidone/vinyl acetate copolymer, and (b) vinylpyrrolidone/vinyl acetate copolymer dissolved in a solvent, exhibit a synergistic effect of lowering the exposure of ozone transmission through the topical composition.

The vinylpyrrolidone/vinyl acetate copolymer is a linear, random copolymer produced by the free-radical polymerization of vinylpyrrolidone monomers and vinyl acetate monomers in a particular ratio.

Vinylpyrrolidone/vinyl acetate copolymer may be abbreviated as PVP/VA, or PVP/VA copolymer, and may be known as poly(1-vinylpyrrolidone-co-vinyl acetate).

The vinylpyrrolidone/vinyl acetate copolymer has the formula $-[CH_2-CHR]_x-$, wherein R is either a pyrrolidone bound to the polymer chain via the pyrrolidone's nitrogen, or an acetate group. The variable x varies with the molecular length, but is generally roughly 200 to 1000. Alternatively, vinylpyrrolidone/vinyl acetate copolymer has the formula $-[CH_2CHY]_m[CH_2=CH(-CO-CH_3)]_n-$, wherein Y is a pyrrolidone bound to the polymer chain via the pyrrolidone's nitrogen.

A pyrrolidone consists of a five-membered ring containing an amide group. Vinylpyrrolidone consists of a five-membered ring containing an amide group, wherein the nitrogen of the amide group is further bonded to a vinyl group.

An acetate group consists of the group $-O-CO-CH_3$.

The vinylpyrrolidone/vinyl acetate copolymer may be obtained from any suitable commercial source, including Ashland, BASF, GAF Materials Corp., Shanghai Yuking Water Soluble Material Tech Co., Dalian Sinobio Chemistry Co., and Hefei Joye Import & Export Co.

The present invention is related to a topical composition prepared by mixing sequentially into a skin lotion (a) solid vinylpyrrolidone/vinyl acetate copolymer, and (b) vinylpyrrolidone/vinyl acetate copolymer dissolved in a solvent.

The solid vinylpyrrolidone/vinyl acetate copolymer may be a powder, microspheres, flakes, or pellets. Under one embodiment the solid vinylpyrrolidone/vinyl acetate copolymer is a powder.

The vinylpyrrolidone/vinyl acetate copolymer dissolved in a solvent may be dissolved in a weight ratio range of about 40 wt % to about 60 wt %. Under one embodiment, the vinylpyrrolidone/vinyl acetate copolymer is dissolved in the solvent at about 50 wt %.

Under one embodiment, the solid vinylpyrrolidone/vinyl acetate copolymer is the same as the vinylpyrrolidone/vinyl acetate copolymer dissolved in a solvent. Under another embodiment, the solid vinylpyrrolidone/vinyl acetate copolymer is similar to the vinylpyrrolidone/vinyl acetate copolymer dissolved in a solvent. Under another embodiment, the solid vinylpyrrolidone/vinyl acetate copolymer is different from the vinylpyrrolidone/vinyl acetate copolymer dissolved in a solvent.

The phrase "solid vinylpyrrolidone/vinyl acetate copolymer" is meant to indicate that that particular vinylpyrrolidone/vinyl acetate copolymer was added to the skin lotion as a solid, and not to indicate that the vinylpyrrolidone/vinyl acetate copolymer is necessarily a solid in the lotion. Similarly, the phrase "vinylpyrrolidone/vinyl acetate copolymer dissolved in a solvent" is meant to indicate that that particular vinylpyrrolidone/vinyl acetate copolymer was added to the skin lotion dissolved in a solvent, and not to indicate that the vinylpyrrolidone/vinyl acetate copolymer is necessarily in the solvent in the lotion. The modifier term "solid" in the phrase "solid vinylpyrrolidone/vinyl acetate copolymer" and the modifier phrase "dissolved in a solvent" in the phrase "vinylpyrrolidone/vinyl acetate copolymer dissolved in a solvent" are indications of the origin of the copolymer in each instance, and not necessarily of the state thereof in the lotion.

The molecular weight of the vinylpyrrolidone/vinyl acetate copolymer is in the range of about 10,000 g/mol to about 100,000 g/mol. This refers to the solid vinylpyrrolidone/vinyl acetate copolymer, to the vinylpyrrolidone/vinyl acetate copolymer dissolved in a solvent, and both of the vinylpyrrolidone/vinyl acetate copolymers.

Under an embodiment, the solid vinylpyrrolidone/vinyl acetate copolymer has a molecular weight in the range of about 10,000 g/mol to about 100,000 g/mol. Under an embodiment, the solid vinylpyrrolidone/vinyl acetate copolymer has a molecular weight in the range of about 10,000 g/mol to about 90,000 g/mol. Under an embodiment, the solid vinylpyrrolidone/vinyl acetate copolymer has a molecular weight in the range of about 10,000 g/mol to about 80,000 g/mol. Under an embodiment, the solid vinylpyrrolidone/vinyl acetate copolymer has a molecular weight in the range of about 10,000 g/mol to about 70,000 g/mol. Under an embodiment, the solid vinylpyrrolidone/vinyl acetate copolymer has a molecular weight in the range of about 10,000 g/mol to about 60,000 g/mol. Under an embodiment, the solid vinylpyrrolidone/vinyl acetate copolymer has a molecular weight in the range of about 10,000 g/mol to about 50,000 g/mol. Under an embodiment, the solid vinylpyrrolidone/vinyl acetate copolymer has a molecular weight in the range of about 10,000 g/mol to about 40,000 g/mol. Under an embodiment, the solid vinylpyrrolidone/vinyl acetate copolymer has a molecular weight in the range of about 10,000 g/mol to about 30,000 g/mol. Under an embodiment, the solid vinylpyrrolidone/vinyl acetate copolymer has a molecular weight in the range of about 10,000 g/mol to about 20,000 g/mol.

Under an embodiment, the solid vinylpyrrolidone/vinyl acetate copolymer has a molecular weight in the range of about 20,000 g/mol to about 100,000 g/mol. Under an embodiment, the solid vinylpyrrolidone/vinyl acetate copolymer has a molecular weight in the range of about 20,000 g/mol to about 90,000 g/mol. Under an embodiment, the solid vinylpyrrolidone/vinyl acetate copolymer has a molecular weight in the range of about 20,000 g/mol to about 80,000 g/mol. Under an embodiment, the solid vinylpyrrolidone/vinyl acetate copolymer has a molecular weight in the range of about 20,000 g/mol to about 70,000 g/mol. Under an embodiment, the solid vinylpyrrolidone/vinyl acetate copolymer has a molecular weight in the range of about 20,000 g/mol to about 60,000 g/mol. Under an embodiment, the solid vinylpyrrolidone/vinyl acetate copolymer has a molecular weight in the range of about 20,000 g/mol to about 50,000 g/mol. Under an embodiment, the solid vinylpyrrolidone/vinyl acetate copolymer has a molecular weight in the range of about 20,000 g/mol to about 40,000 g/mol. Under an embodiment, the solid vinylpyrrolidone/vinyl acetate copolymer has a molecular weight in the range of about 20,000 g/mol to about 30,000 g/mol.

Under an embodiment, the solid vinylpyrrolidone/vinyl acetate copolymer has a molecular weight in the range of about 30,000 g/mol to about 100,000 g/mol. Under an embodiment, the solid vinylpyrrolidone/vinyl acetate copolymer has a molecular weight in the range of about 30,000 g/mol to about 90,000 g/mol. Under an embodiment, the solid vinylpyrrolidone/vinyl acetate copolymer has a molecular weight in the range of about 30,000 g/mol to about 80,000 g/mol. Under an embodiment, the solid vinylpyrrolidone/vinyl acetate copolymer has a molecular weight in the range of about 30,000 g/mol to about 70,000 g/mol. Under an embodiment, the solid vinylpyrrolidone/vinyl acetate copolymer has a molecular weight in the range of about 30,000 g/mol to about 60,000 g/mol. Under an embodiment, the solid vinylpyrrolidone/vinyl acetate copolymer has a molecular weight in the range of about 30,000 g/mol to about 50,000 g/mol. Under an embodiment, the solid vinylpyrrolidone/vinyl acetate copolymer has a molecular weight in the range of about 30,000 g/mol to about 40,000 g/mol.

Under an embodiment, the solid vinylpyrrolidone/vinyl acetate copolymer has a molecular weight in the range of about 40,000 g/mol to about 100,000 g/mol. Under an embodiment, the solid vinylpyrrolidone/vinyl acetate copolymer has a molecular weight in the range of about 40,000 g/mol to about 90,000 g/mol. Under an embodiment, the solid vinylpyrrolidone/vinyl acetate copolymer has a molecular weight in the range of about 40,000 g/mol to about 80,000 g/mol. Under an embodiment, the solid vinylpyrrolidone/vinyl acetate copolymer has a molecular weight in the range of about 40,000 g/mol to about 70,000 g/mol. Under an embodiment, the solid vinylpyrrolidone/vinyl acetate copolymer has a molecular weight in the range of about 40,000 g/mol to about 60,000 g/mol. Under an embodiment, the solid vinylpyrrolidone/vinyl acetate copolymer has a molecular weight in the range of about 40,000 g/mol to about 50,000 g/mol.

Under an embodiment, the solid vinylpyrrolidone/vinyl acetate copolymer has a molecular weight in the range of about 50,000 g/mol to about 100,000 g/mol. Under an embodiment, the solid vinylpyrrolidone/vinyl acetate copolymer has a molecular weight in the range of about 50,000 g/mol to about 90,000 g/mol. Under an embodiment, the solid vinylpyrrolidone/vinyl acetate copolymer has a molecular weight in the range of about 50,000 g/mol to about 80,000 g/mol. Under an embodiment, the solid vinylpyrrolidone/vinyl acetate copolymer has a molecular weight in the range of about 50,000 g/mol to about 70,000 g/mol. Under an embodiment, the solid vinylpyrrolidone/vinyl acetate copolymer has a molecular weight in the range of about 50,000 g/mol to about 60,000 g/mol.

Under an embodiment, the solid vinylpyrrolidone/vinyl acetate copolymer has a molecular weight in the range of about 60,000 g/mol to about 100,000 g/mol. Under an embodiment, the solid vinylpyrrolidone/vinyl acetate copolymer has a molecular weight in the range of about 60,000 g/mol to about 90,000 g/mol. Under an embodiment, the solid vinylpyrrolidone/vinyl acetate copolymer has a molecular weight in the range of about 60,000 g/mol to about 80,000 g/mol. Under an embodiment, the solid vinylpyrrolidone/vinyl acetate copolymer has a molecular weight in the range of about 60,000 g/mol to about 70,000 g/mol.

Under an embodiment, the solid vinylpyrrolidone/vinyl acetate copolymer has a molecular weight in the range of about 70,000 g/mol to about 100,000 g/mol. Under an embodiment, the solid vinylpyrrolidone/vinyl acetate copolymer has a molecular weight in the range of about 70,000 g/mol to about 90,000 g/mol. Under an embodiment, the solid vinylpyrrolidone/vinyl acetate copolymer has a molecular weight in the range of about 70,000 g/mol to about 80,000 g/mol. Under an embodiment, the solid vinylpyrrolidone/vinyl acetate copolymer has a molecular weight in the range of about 80,000 g/mol to about 100,000 g/mol. Under an embodiment, the solid vinylpyrrolidone/vinyl acetate copolymer has a molecular weight in the range of about 80,000 g/mol to about 90,000 g/mol. Under an embodiment, the solid vinylpyrrolidone/vinyl acetate copolymer has a molecular weight in the range of about 90,000 g/mol to about 100,000 g/mol.

Under an embodiment, the vinylpyrrolidone/vinyl acetate copolymer dissolved in a solvent has a molecular weight in the range of about 10,000 g/mol to about 100,000 g/mol. Under an embodiment, the vinylpyrrolidone/vinyl acetate copolymer dissolved in a solvent has a molecular weight in the range of about 10,000 g/mol to about 90,000 g/mol. Under an embodiment, the vinylpyrrolidone/vinyl acetate copolymer dissolved in a solvent has a molecular weight in the range of about 10,000 g/mol to about 80,000 g/mol. Under an embodiment, the vinylpyrrolidone/vinyl acetate copolymer dissolved in a solvent has a molecular weight in the range of about 10,000 g/mol to about 70,000 g/mol. Under an embodiment, the vinylpyrrolidone/vinyl acetate copolymer dissolved in a solvent has a molecular weight in the range of about 10,000 g/mol to about 60,000 g/mol. Under an embodiment, the vinylpyrrolidone/vinyl acetate copolymer dissolved in a solvent has a molecular weight in the range of about 10,000 g/mol to about 50,000 g/mol. Under an embodiment, the vinylpyrrolidone/vinyl acetate copolymer dissolved in a solvent has a molecular weight in the range of about 10,000 g/mol to about 40,000 g/mol. Under an embodiment, the vinylpyrrolidone/vinyl acetate copolymer dissolved in a solvent has a molecular weight in the range of about 10,000 g/mol to about 30,000 g/mol. Under an embodiment, the vinylpyrrolidone/vinyl acetate copolymer dissolved in a solvent has a molecular weight in the range of about 10,000 g/mol to about 20,000 g/mol.

Under an embodiment, the vinylpyrrolidone/vinyl acetate copolymer dissolved in a solvent has a molecular weight in the range of about 20,000 g/mol to about 100,000 g/mol. Under an embodiment, the vinylpyrrolidone/vinyl acetate copolymer dissolved in a solvent has a molecular weight in the range of about 20,000 g/mol to about 90,000 g/mol. Under an embodiment, the vinylpyrrolidone/vinyl acetate copolymer dissolved in a solvent has a molecular weight in the range of about 20,000 g/mol to about 80,000 g/mol. Under an embodiment, the vinylpyrrolidone/vinyl acetate copolymer dissolved in a solvent has a molecular weight in the range of about 20,000 g/mol to about 70,000 g/mol. Under an embodiment, the vinylpyrrolidone/vinyl acetate copolymer dissolved in a solvent has a molecular weight in the range of about 20,000 g/mol to about 60,000 g/mol. Under an embodiment, the vinylpyrrolidone/vinyl acetate copolymer dissolved in a solvent has a molecular weight in the range of about 20,000 g/mol to about 50,000 g/mol. Under an embodiment, the vinylpyrrolidone/vinyl acetate copolymer dissolved in a solvent has a molecular weight in the range of about 20,000 g/mol to about 40,000 g/mol. Under an embodiment, the vinylpyrrolidone/vinyl acetate copolymer dissolved in a solvent has a molecular weight in the range of about 20,000 g/mol to about 30,000 g/mol.

Under an embodiment, the vinylpyrrolidone/vinyl acetate copolymer dissolved in a solvent has a molecular weight in the range of about 30,000 g/mol to about 100,000 g/mol. Under an embodiment, the vinylpyrrolidone/vinyl acetate copolymer dissolved in a solvent has a molecular weight in the range of about 30,000 g/mol to about 90,000 g/mol. Under an embodiment, the vinylpyrrolidone/vinyl acetate copolymer dissolved in a solvent has a molecular weight in the range of about 30,000 g/mol to about 80,000 g/mol. Under an embodiment, the vinylpyrrolidone/vinyl acetate copolymer dissolved in a solvent has a molecular weight in the range of about 30,000 g/mol to about 70,000 g/mol. Under an embodiment, the vinylpyrrolidone/vinyl acetate copolymer dissolved in a solvent has a molecular weight in the range of about 30,000 g/mol to about 60,000 g/mol. Under an embodiment, the vinylpyrrolidone/vinyl acetate copolymer dissolved in a solvent has a molecular weight in the range of about 30,000 g/mol to about 50,000 g/mol. Under an embodiment, the vinylpyrrolidone/vinyl acetate copolymer dissolved in a solvent has a molecular weight in the range of about 30,000 g/mol to about 40,000 g/mol.

Under an embodiment, the vinylpyrrolidone/vinyl acetate copolymer dissolved in a solvent has a molecular weight in the range of about 40,000 g/mol to about 100,000 g/mol. Under an embodiment, the vinylpyrrolidone/vinyl acetate copolymer dissolved in a solvent has a molecular weight in the range of about 40,000 g/mol to about 90,000 g/mol. Under an embodiment, the vinylpyrrolidone/vinyl acetate copolymer dissolved in a solvent has a molecular weight in the range of about 40,000 g/mol to about 80,000 g/mol. Under an embodiment, the vinylpyrrolidone/vinyl acetate copolymer dissolved in a solvent has a molecular weight in the range of about 40,000 g/mol to about 70,000 g/mol. Under an embodiment, the vinylpyrrolidone/vinyl acetate copolymer dissolved in a solvent has a molecular weight in the range of about 40,000 g/mol to about 60,000 g/mol. Under an embodiment, the vinylpyrrolidone/vinyl acetate copolymer dissolved in a solvent has a molecular weight in the range of about 40,000 g/mol to about 50,000 g/mol.

Under an embodiment, the vinylpyrrolidone/vinyl acetate copolymer dissolved in a solvent has a molecular weight in the range of about 50,000 g/mol to about 100,000 g/mol. Under an embodiment, the vinylpyrrolidone/vinyl acetate copolymer dissolved in a solvent has a molecular weight in the range of about 50,000 g/mol to about 90,000 g/mol. Under an embodiment, the vinylpyrrolidone/vinyl acetate copolymer dissolved in a solvent has a molecular weight in the range of about 50,000 g/mol to about 80,000 g/mol. Under an embodiment, the vinylpyrrolidone/vinyl acetate copolymer dissolved in a solvent has a molecular weight in the range of about 50,000 g/mol to about 70,000 g/mol. Under an embodiment, the vinylpyrrolidone/vinyl acetate copolymer dissolved in a solvent has a molecular weight in the range of about 50,000 g/mol to about 60,000 g/mol.

Under an embodiment, the vinylpyrrolidone/vinyl acetate copolymer dissolved in a solvent has a molecular weight in the range of about 60,000 g/mol to about 100,000 g/mol. Under an embodiment, the vinylpyrrolidone/vinyl acetate copolymer dissolved in a solvent has a molecular weight in the range of about 60,000 g/mol to about 90,000 g/mol. Under an embodiment, the vinylpyrrolidone/vinyl acetate copolymer dissolved in a solvent has a molecular weight in the range of about 60,000 g/mol to about 80,000 g/mol. Under an embodiment, the vinylpyrrolidone/vinyl acetate copolymer dissolved in a solvent has a molecular weight in the range of about 60,000 g/mol to about 70,000 g/mol.

Under an embodiment, the vinylpyrrolidone/vinyl acetate copolymer dissolved in a solvent has a molecular weight in the range of about 70,000 g/mol to about 100,000 g/mol. Under an embodiment, the vinylpyrrolidone/vinyl acetate copolymer dissolved in a solvent has a molecular weight in the range of about 70,000 g/mol to about 90,000 g/mol. Under an embodiment, the vinylpyrrolidone/vinyl acetate copolymer dissolved in a solvent has a molecular weight in the range of about 70,000 g/mol to about 80,000 g/mol. Under an embodiment, the vinylpyrrolidone/vinyl acetate copolymer dissolved in a solvent has a molecular weight in the range of about 80,000 g/mol to about 100,000 g/mol. Under an embodiment, the vinylpyrrolidone/vinyl acetate copolymer dissolved in a solvent has a molecular weight in the range of about 80,000 g/mol to about 90,000 g/mol. Under an embodiment, the vinylpyrrolidone/vinyl acetate copolymer dissolved in a solvent has a molecular weight in the range of about 90,000 g/mol to about 100,000 g/mol.

The weight ratio of the vinylpyrrolidone units to vinyl acetate units present in each vinylpyrrolidone/vinyl acetate copolymer is determined during the preparation of the copolymer.

Under an embodiment, the weight ratio of the vinylpyrrolidone units to vinyl acetate units present in the solid vinylpyrrolidone/vinyl acetate copolymer is in the range of about 20:80 to 80:20. Under an embodiment, the weight ratio of the vinylpyrrolidone units to vinyl acetate units present in the solid vinylpyrrolidone/vinyl acetate copolymer is in the range of about 30:70 to 50:50. Under an embodiment, the weight ratio of the vinylpyrrolidone units to vinyl acetate units present in the solid vinylpyrrolidone/vinyl acetate copolymer is in the range of about 50:50 to 70:30. Under an embodiment, the weight ratio of the vinylpyrrolidone units to vinyl acetate units present in the vinylpyrrolidone/vinyl acetate copolymer dissolved in a solvent is in the range of about 20:80 to 80:20. Under an embodiment, the weight ratio of the vinylpyrrolidone units to vinyl acetate units present in the vinylpyrrolidone/vinyl acetate copolymer dissolved in a solvent is in the range of about 30:70 to 50:50. Under an embodiment, the weight ratio of the vinylpyrrolidone units to vinyl acetate units present in the vinylpyrrolidone/vinyl acetate copolymer dissolved in a solvent is in the range of about 50:50 to 70:30.

The present invention is related to a topical composition prepared by mixing sequentially into a skin lotion (a) solid vinylpyrrolidone/vinyl acetate copolymer, and (b) vinylpyrrolidone/vinyl acetate copolymer dissolved in a solvent. Under some embodiments, the amounts of the polymer contents of (a) and (b) are about equal. Under other embodiments, the amount of the polymer contents of (a) is greater than the amount of the polymer contents of (b). Under other embodiments, the amount of the polymer contents of (a) is less than the amount of the polymer contents of (b).

The phrase "the weight ratio of copolymer content of (a) to (b)" means the ratio the weight of the solid vinylpyrrolidone/vinyl acetate copolymer to the weight of the vinylpyrrolidone/vinyl acetate copolymer that is present in the solution of the vinylpyrrolidone/vinyl acetate copolymer dissolved in a solvent. This means that the ratios are of the copolymers themselves, adjusting for the solvent. Thus, for example, if the loading level of the solid vinylpyrrolidone/vinyl acetate copolymer is 1.0 wt % and the loading level of the vinylpyrrolidone/vinyl acetate copolymer dissolved in a solvent is also 1.0 wt %, wherein the solution of the vinylpyrrolidone/vinyl acetate copolymer dissolved in a solvent and the solvent comprise 50 wt % of vinylpyrrolidone/vinyl acetate copolymer; then the effective loading levels, adjusted for the solvent, are 1.0 wt %:0.50 wt %, or 2:1.

Under an embodiment, the weight ratio of the copolymer contents of (a) to (b) is about 8:1 to about 0.4:1. Under an embodiment, the weight ratio of the copolymer contents of (a) to (b) is about 8:1 to about 0.5:1. Under an embodiment, the weight ratio of the copolymer contents of (a) to (b) is about 8:1 to about 0.67:1. Under an embodiment, the weight ratio of the copolymer contents of (a) to (b) is about 8:1 to about 0.8:1. Under an embodiment, the weight ratio of the copolymer contents of (a) to (b) is about 8:1 to about 1:1. Under an embodiment, the weight ratio of the copolymer contents of (a) to (b) is about 8:1 to about 2:1. Under an embodiment, the weight ratio of the copolymer contents of (a) to (b) is about 8:1 to about 3:1. Under an embodiment, the weight ratio of the copolymer contents of (a) to (b) is about 8:1 to about 4:1. Under an embodiment, the weight ratio of the copolymer contents of (a) to (b) is about 8:1 to about 6:1.

Under an embodiment, the weight ratio of the copolymer contents of (a) to (b) is about 6:1 to about 0.4:1. Under an embodiment, the weight ratio of the copolymer contents of (a) to (b) is about 6:1 to about 0.5:1. Under an embodiment, the weight ratio of the copolymer contents of (a) to (b) is about 6:1 to about 0.67:1. Under an embodiment, the weight ratio of the copolymer contents of (a) to (b) is about 6:1 to about 0.8:1. Under an embodiment, the weight ratio of the copolymer contents of (a) to (b) is about 6:1 to about 1:1. Under an embodiment, the weight ratio of the copolymer contents of (a) to (b) is about 6:1 to about 2:1. Under an embodiment, the weight ratio of the copolymer contents of (a) to (b) is about 6:1 to about 3:1. Under an embodiment, the weight ratio of the copolymer contents of (a) to (b) is about 6:1 to about 4:1.

Under an embodiment, the weight ratio of the copolymer contents of (a) to (b) is about 4:1 to about 0.4:1. Under an embodiment, the weight ratio of the copolymer contents of (a) to (b) is about 4:1 to about 0.5:1. Under an embodiment, the weight ratio of the copolymer contents of (a) to (b) is about 4:1 to about 0.67:1. Under an embodiment, the weight ratio of the copolymer contents of (a) to (b) is about 4:1 to about 0.8:1. Under an embodiment, the weight ratio of the copolymer contents of (a) to (b) is about 4:1 to about 1:1. Under an embodiment, the weight ratio of the copolymer contents of (a) to (b) is about 4:1 to about 2:1. Under an embodiment, the weight ratio of the copolymer contents of (a) to (b) is about 4:1 to about 3:1.

Under an embodiment, the weight ratio of the copolymer contents of (a) to (b) is about 3:1 to about 0.4:1. Under an embodiment, the weight ratio of the copolymer contents of (a) to (b) is about 3:1 to about 0.5:1. Under an embodiment, the weight ratio of the copolymer contents of (a) to (b) is about 3:1 to about 0.67:1. Under an embodiment, the weight ratio of the copolymer contents of (a) to (b) is about 3:1 to about 0.8:1. Under an embodiment, the weight ratio of the copolymer contents of (a) to (b) is about 3:1 to about 1:1. Under an embodiment, the weight ratio of the copolymer contents of (a) to (b) is about 3:1 to about 2:1.

Under an embodiment, the weight ratio of the copolymer contents of (a) to (b) is about 2:1 to about 0.4:1. Under an embodiment, the weight ratio of the copolymer contents of (a) to (b) is about 2:1 to about 0.5:1. Under an embodiment, the weight ratio of the copolymer contents of (a) to (b) is about 2:1 to about 0.67:1. Under an embodiment, the weight ratio of the copolymer contents of (a) to (b) is about 2:1 to about 0.8:1. Under an embodiment, the weight ratio of the copolymer contents of (a) to (b) is about 2:1 to about 1:1.

Under an embodiment, the weight ratio of the copolymer contents of (a) to (b) is about 1:1 to about 0.4:1. Under an embodiment, the weight ratio of the copolymer contents of (a) to (b) is about 1:1 to about 0.5:1. Under an embodiment, the weight ratio of the copolymer contents of (a) to (b) is about 1:1 to about 0.67:1. Under an embodiment, the weight ratio of the copolymer contents of (a) to (b) is about 1:1 to about 0.8:1.

Under an embodiment, the weight ratio of the copolymer contents of (a) to (b) is about 0.8:1 to about 0.4:1. Under an embodiment, the weight ratio of the copolymer contents of (a) to (b) is about 0.8:1 to about 0.5:1. Under an embodiment, the weight ratio of the copolymer contents of (a) to (b) is about 0.8:1 to about 0.67:1. Under an embodiment, the weight ratio of the copolymer contents of (a) to (b) is about 0.67:1 to about 0.4:1. Under an embodiment, the weight ratio of the copolymer contents of (a) to (b) is about 0.67:1 to about 0.5:1. Under an embodiment, the weight ratio of the copolymer contents of (a) to (b) is about 0.5:1 to about 0.4:1.

The present invention is related to a topical composition prepared by mixing sequentially into a skin lotion (a) solid vinylpyrrolidone/vinyl acetate copolymer, and (b) vinylpyrrolidone/vinyl acetate copolymer dissolved in a solvent. The definition of the term "solvent" includes any fluid which fully solubilizes the vinylpyrrolidone/vinyl acetate copolymer of (b). Under one embodiment, the solvent is cosmetically acceptable solvent.

Vinylpyrrolidone/vinyl acetate copolymers dissolve in polar solvents. These solvent include solvents that are small organic compounds which contain atoms with lone pairs, such as oxygen, or nitrogen. The solvent should not have a high degree of hydrocarbon-like characteristic. Acceptable solvents include alcohols, esters, ketones, and water.

Under one embodiment, the solvent is selected from the group consisting of alcohols, esters, and ketones.

Alcohols include primary and secondary alcohols. Examples of alcohol include methanol, $CH_3OH$, ethanol, $CH_3—CH_2—OH$, n-propanol, $CH_3—CH_2—CH_2—OH$, i-propanol, isopropanol, $CH_3—CH(OH)—CH_3$, and mixtures thereof.

Esters include methyl acetate, $CH_3—CO—O—CH_3$, ethyl acetate, $CH_3—CO—O—CH_2—CH_3$, methyl propionate, $CH_3—CH_2—CO—O—CH_3$, ethyl propionate, $CH_3—CH_2—CO—O—CH_2—CH_3$, and mixtures thereof.

Ketones include acetone, $CH_3—CO—CH_3$, methyl ethyl ketone, $CH_3—CO—CH_2—CH_3$, 3-pentone, $CH_3—CH_2—CO—CH_2—CH_3$, and mixtures thereof.

Under one embodiment, the solvent is ethanol.

The present invention is related to a topical composition for use in reducing exposure of gaseous pollutants to the skin, prepared by mixing sequentially into a skin lotion (a) solid vinylpyrrolidone/vinyl acetate copolymer, and (b) vinylpyrrolidone/vinyl acetate copolymer dissolved in a solvent. The balance of the topical composition is any topical composition that is compatible with both vinylpyrrolidone/vinyl acetate copolymers.

The topical composition may be a skin lotion. A skin lotion is a stable or semi-stable mixture of oils, water, and ingredients miscible therein. The ingredient with the highest loading level is usually water. The oils may be used to provide moisturizing effects to the patient's skin. Moisturization can happen in a variety of ways including changing the feel of the skin, attracting water to the skin, and blocking water from escaping the skin. When put on the skin, the lotion interacts with the skin surface to provide a soothing feeling. Over time, the occlusive agents in the lotion prevent water from leaving the skin which helps build moisture in the skin. This additional moisture ultimately mitigates the problems associated with dry skin.

The mixture of water, oil, and other ingredients that form skin lotion are formulated to provide a homogeneous mixture, such as an emulsion. Additional ingredients include ingredients that may be described by their function in the emulsion, such as diluents, thickeners, humectants, preservatives, neutralizers, emulsifiers, co-emulsifiers, emollients, occlusive agents, fragrances, and colorants. Some ingredients may have more than function in the skin lotion.

Common moisturizing ingredients are occlusive agents which create a barrier that blocks water from escaping the skin. Examples of occlusive agents include petrolatum, fatty alcohols (such as cetyl alcohol and stearyl alcohol), hydrocarbon oils (such as mineral oil), silicones (such as dimethicone and cyclomethicone), squalene, wax esters (such as beeswax and lanolin; vegetable waxes (such as candelilla, carnauba, and palm kernel), plant-based oils (such as olive, rice bran, macadamia, castor, soybean oil, shea butter), cholesterol, and lecithin.

The lotion may include a humectant, which is an ingredient that attracts water. The humectant attracts and retains the moisture in the air nearby via absorption, drawing the water vapor into or beneath the surface of the upper layer of the patient's skin. Humectants generally have hydroxyl groups which allow them to participate in hydrogen bonding and attract water. This process attracts moisture from the outer layer of the skin or, in high humidity, from the atmosphere. The moisture is then trapped against the epidermis. Examples of humectants include triethylene glycol, tripropylene glycol, propylene glycol, glycerin, polyethylene glycols, PPG, glycerin, sorbitol, hexylene glycol, butylene glycol, urea, silicones, collagen, aloe, honey, and hyaluronic acid.

The lotion may also include an emollient. An emollient is an ingredient that improves the feel of the lotion on the skin. An emollient may reduce the tackiness and greasiness caused by the other moisturizing ingredients. Examples of common emollients include coconut oil, cetyl esters, selected silicones oils, shea butter, cocoa butter, mineral oil, lanolin, petrolatum, paraffin, beeswax, squalene, coconut oil, jojoba oil, sesame oil, almond oil, cetyl alcohol, olive oil, oleic acid, and triethylhexanoin.

The lotion may also comprise an emulsifier. An emulsifier is an ingredient that improves the stability of the mixture of oil materials and water. Examples of common emulsifiers include, glyceryl stearate and stearic acid. Additional examples of emulsifiers include acacia seyal gum octenylsuccinate, $C_{12-18}$-acid triglyceride, acrylates crosspolymer-4, *Adansonia digitata* seed oil peg-8 esters, *Adansonia digitata* seed oil polyglyceryl-6 esters, almond oil glyceryl-8 esters, almond oil peg-6 esters, almond oil peg-8 esters, sweet almond oil peg-8 esters, sweet almond oil polyglyceryl-4 esters, sweet almond oil polyglyceryl-6 esters, aluminum lanolate, ammonium $C_{6-16}$ perfluoroalkylethyl phosphate, ammonium coco-sulfate, ammonium isostearate, ammonium oleate, ammonium perfluorohexyl ethylphosphates, ammonium shellacate, ammonium stearate, ammonium tallate, AMPD-isostearoyl hydrolyzed collagen, AMPD-rosin hydrolyzed collagen, apricot kernel oil peg-6 esters, apricot kernel oil peg-8 esters, apricot kernel oil peg-40 esters, apricot kernel oil polyglyceryl-3 esters, apricot kernel oil polyglyceryl-4 esters, apricot kernel oil polyglyceryl-5 esters, apricot kernel oil polyglyceryl-6 esters, apricot kernel oil polyglyceryl-10 esters, arachideth-20, arachidic acid, arachidyl glucoside, argan oil peg-8 esters, argan oil polyglyceryl-6 esters, *Astrocaryum vulgare* oil polyglyceryl-6 esters, avocadamide DEA, avocadamide DIPA, avocado oil peg-8 esters, avocado oil propylene glycol esters, babassu oil glycereth-8 esters, babassu oil polyglyceryl-6 esters, babassuamidopropyltrimonium chloride, babassuamidopropyltrimonium methosulfate, behenamidopropyl dimethylamine, beheneth-2, beheneth-5, beheneth-10, beheneth-15, beheneth-20, beheneth-25, beheneth-30, behenoyl stearic acid, behenyl PG-trimonium chloride, benzenesulfonyltromethamide, *Bertholletia excelsa* seed oil polyglyceryl-6 esters, borage seed oil peg-8 esters, borage seed oil polyglyceryl-4 esters, borage seed oil polyglyceryl-6 esters, butoxynol-19 carboxylic acid, butoxynol-5 carboxylic acid, butyl octanoic acid, bis-iso butyl peg/ppg-10/7/dimethicone copolymer, bis-butyldimethicone polyglyceryl-3, butyldimoniumhydroxypropyl butylglucosides chloride, butyldimoniumhydroxypropyl laurylglucosides chloride, butylene glycol behenate, butylene glycol cocoate, butylene glycol isostearate, butylene glycol isostearates, butylene glycol laurate, butylene glycol myristate, butylene glycol stearate, butylglucoside caprate, butylglucosides hydroxypropyltrimonium chloride, $C_{1-5}$ alkyl galactomannan, $C_{10-16}$ alkyl glucoside, $C_{10-18}$ triglycerides polyglyceryl-3 esters phosphates, $C_{10-30}$ cholesterol/lanosterol esters, $C_{10-40}$ isoalkyl acid glyceride, $C_{11-13}$ pareth-6, $C_{11-13}$ pareth-9, $C_{11-13}$ pareth-10, $C_{11-15}$ pareth-3, $C_{11-15}$ pareth-5, $C_{11-15}$ pareth-7, $C_{11-15}$ pareth-9, $C_{11-15}$ pareth-12, $C_{11-15}$ pareth-15, $C_{11-15}$ pareth-20, $C_{11-15}$ pareth-30, $C_{11-15}$ pareth-3 oleate, $C_{11-15}$ pareth-7 carboxylic acid, $C_{11-15}$ sec-pareth-12, $C_{11-21}$ pareth-3, $C_{11-21}$ pareth-10, $C_{12-13}$ pareth-2, $C_{12-13}$ pareth-3, $C_{12-13}$ pareth-4, $C_{12-13}$ pareth-5, $C_{12-13}$ pareth-6, $C_{12-13}$ pareth-7, $C_{12-13}$ pareth-9, $C_{12-13}$ pareth-10, $C_{12-13}$ pareth-15, $C_{12-13}$ pareth-23, $C_{12-13}$ pareth-10 phosphate, $C_{12-14}$ alkyl diaminoethylglycine HCl, $C_{12-14}$ pareth-7, $C_{12-14}$ pareth-12, $C_{12-14}$ pareth-3, $C_{12-14}$ sec-pareth-3, $C_{12-14}$ sec-pareth-5, $C_{12-14}$ sec-pareth-7, $C_{12-14}$ sec-pareth-8, $C_{12-14}$ sec-pareth-9, $C_{12-14}$ sec-pareth-12, $C_{12-14}$ sec-pareth-15, $C_{12-14}$ sec-pareth-20, $C_{12-14}$ sec-pareth-30, $C_{12-14}$ sec-pareth-40, $C_{12-14}$ sec-pareth-50, $C_{12-15}$ pareth-12, $C_{12-13}$ pareth-2, $C_{12-15}$ pareth-2 phosphate, $C_{12-15}$ pareth-3 phosphate, $C_{12-15}$ pareth-4, $C_{12-15}$ pareth-5, $C_{12-15}$ pareth-6 phosphate, $C_{12-15}$ pareth-8 carboxylic acid, $C_{12-15}$ pareth-8 phosphate, $C_{12-15}$ pareth-9 phosphate, $C_{12-15}$ pareth-10, $C_{12-15}$ pareth-10 phosphate, $C_{12-15}$ pareth-11, $C_{12-15}$ pareth-3, $C_{12-15}$ pareth-7, $C_{12-15}$ pareth-9, $C_{12-15}$ pareth-9 hydrogenated tallowate, $C_{12-16}$ pareth-5, $C_{12-16}$ pareth-6 phosphate, $C_{12-16}$ pareth-7, $C_{12-16}$ pareth-9, $C_{12-20}$ acid peg-8 ester, $C_{12-20}$ alkyl glucoside, $C_{14-15}$ pareth-4, $C_{14-15}$ pareth-7, $C_{14-15}$ pareth-11, $C_{14-15}$ pareth-12, $C_{14-15}$ pareth-13, $C_{14-16}$ glycol palmitate, $C_{18-20}$ glycol isostearate, $C_{18-36}$ acid, $C_{18-36}$ acid glycol ester, $C_{20-22}$ alkyl phosphate, $C_{20-22}$ pareth-30, $C_{20-40}$ alcohols, $C_{20-40}$ pareth-3, $C_{20-40}$ pareth-10, $C_{20-40}$ pareth-24, $C_{20-40}$ pareth-40, $C_{22-24}$ pareth-33, $C_{29-70}$ acid, $C_{30-38}$ olefin/isopropyl maleate/MA copolymer, $C_{30-50}$ pareth-3, $C_{30-50}$ pareth-10, $C_{30-50}$ pareth-40, $C_{40-60}$ acid, $C_{40-60}$ alcohols, $C_{40-60}$ pareth-3, $C_{40-60}$ pareth-10, $C_{6-10}$ pareth-4 phosphate, $C_{6-8}$ alkyl $C_{3-6}$ alkyl glucoside dimethicone, $C_{9-11}$ pareth-4, $C_{9-11}$ pareth-6, $C_{9-11}$ pareth-8, $C_{9-11}$ pareth-3, $C_{9-15}$ alkyl phosphate, $C_{9-15}$ pareth-8, $C_{9-16}$ alkane/cycloalkane, calcium stearoyl lactylate, candelilla/jojoba/rice bran polyglyceryl-3 esters, hydrolyzed *Candida bombicola* sophorolipids, *Cannabis sativa* seed oil peg-8 esters, capryl/lauryl wheat bran/straw glycosides, capryleth-4, capryleth-4 carboxylic acid, capryleth-5, capryleth-6 carboxylic acid, capryleth-9 carboxylic acid, caprylic/capric glycerides polyglycerin-10 esters, caprylic/capric triglyceride peg-4 esters, caprylic/capric/succinic triglyceride, caprylyl dimethicone ethoxy glucoside, caprylyl/capryl wheat bran/straw glycosides, caprylyl/capryl xylosides, *Carapa guaianensis* oil peg-8 esters, *Carpotroche brasiliensis* seed acid, hydrogenated castor oil, cera alba wax, ceteareth-2, ceteareth-3, ceteareth-4, ceteareth-5, ceteareth-6, ceteareth-7, ceteareth-8, iso ceteareth-8 stearate, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, ceteareth-33, ceteareth-34, ceteareth-50, ceteareth-60, ceteareth-6 olivate, ceteareth-60 myristyl glycol, cetearyl glucoside, cetearyl palmate, cetearyl wheat bran glycosides, cetearyl wheat straw glycosides, ceteth-1, ceteth-2, ceteth-3, ceteth-4, ceteth-5, iso ceteth-5, ceteth-6, ceteth-7, iso ceteth-7, ceteth-8, ceteth-8 phosphate, ceteth-10, iso ceteth-10, iso ceteth-10 stearate, ceteth-12, iso ceteth-12, ceteth-13, ceteth-14, ceteth-15, iso ceteth-15, ceteth-16, ceteth-17, ceteth-18, ceteth-20, isoceteth-20, ceteth-23, ceteth-24, ceteth-25, iso ceteth-25, ceteth-30, iso ceteth-30, cetoleth-2, cetoleth-4, cetoleth-5, cetoleth-6, cetoleth-10, cetoleth-11, cetoleth-15, cetoleth-18, cetoleth-20, cetoleth-22, cetyl glyceryl ether/glycerin copolymer, cetyl peg-8 dimethicone, cetyl peg/ppg-10/1 dimethicone, cetyl peg/ppg-15/15 butyl ether dimethicone, cetyl peg/ppg-7/3 dimethicone, cetyl phosphate, cetyl pyridinium chloride anhydrous, chimyl stearate, chitosan lauramide hydroxypropyltrimonium chloride, chitosan PCA palmitamide succinamide, chitosan stearamide hydroxypropyltrimonium chloride, cholesterol, cholesteryl C16-18 alkenyl succinate, choleth-5, choleth-10, choleth-15, choleth-20, choleth-24, choleth-30, cocamide DIPA, cocamine, coceth-3, coceth-5, coceth-6, coceth-7, coceth-7 carboxylic acid, coceth-8, coceth-10, coceth-20, coceth-25, coco-oleate estolides, coco/sunfloweramidopropyl betaine, cocoa butter glyceryl esters, cocoglucosides hydroxypropyltrimonium chloride, cocoglycerides, coconut acid, hydrogenated coconut oil peg-10 esters, coconut oil polyglyceryl-6 esters, coconut oil ppg-2-peg-6 esters, cocoyl ethyl glucoside, coffee seed oil peg-8 esters, coffee seed oil polyglyceryl-6 esters, corn oil glycereth-8 esters, acetylated hydrogenated cottonseed glyceride, *Crambe abyssinica* seed oil phytosterol esters, deceth-3, deceth-4, iso deceth-4, deceth-4 phosphate, deceth-5, isodeceth-5, deceth-6, isodeceth-6, deceth-6 phosphate, deceth-7, deceth-8, deceth-9, deceth-10, isodeceth-2 cocoate, decyltetradeceth-5, decyltetradeceth-15, decyltetradeceth-20, decyltetradeceth-25, decyltetradeceth-30, decyltetradeceth-10, di-$C_{12-15}$ pareth-2 phosphate, di-$C_{12-15}$ pareth-4 phosphate, di-$C_{12-15}$ pareth-6 phosphate, di-$C_{12-15}$ pareth-8 phosphate, di-$C_{12-15}$ pareth-10 phosphate, dibehenyl/diarachidyl dimonium chloride, dibehenyldimonium methosulfate, dibutoxymethane, dicapryl/dicaprylyl dimonium chloride, diceteareth-10 phosphate, dicocodimethylamine dilinoleate, didodecyl butanetetracarboxylate, diethyl aminoethyl cocoate, diethylaminoethyl peg-5 laurate, diethylene glycol diisononanoate, digalactosyl glyceryl linoleate/palmitate/oleate, diglycerin/dilinoleic acid/hydroxystearic acid copolymer, diglyceryl sorbitan tetraethylhexanoate, dihydrocholeth-15, dihydrocholeth-20, dihydrocholeth-30, dihydrolanosterol, dihydroxyethyl tallowamine oxide, dilaureth-4 phosphate, dilaureth-7 citrate, dilaureth-10 phosphate, hydrogenated dimer dilinoleth-20, hydrogenated dimer dilinoleth-30, hydrogenated dimer dilinoleth-40, hydrogenated dimer dilinoleth-80, hydrogenated dimer dilinoleth-60, dimethicone peg-7 phosphate, dimethicone peg-7 undecylenate, dimethicone peg-8 avocadoate, dimethicone peg-10 phosphate, dimethicone peg-15 acetate, dimethicone peg/ppg-12/4 phosphate, dimethicone peg/ppg-7/4 phosphate, dimethicone/peg-10 crosspolymer, dimethicone/polyglycerin-3 crosspolymer, dimethoxysilyl ethylenediaminopropyl dimethicone, dimethyl octynediol, dimethyl soyamine, dimethyl stearamine, dimethyl tallowamine, dimyristyl phosphate, dinonoxynol-4 phosphate, dinonoxynol-9 citrate, dioctyldodecyl stearoyl glutamate, dioleth-8 phosphate, dipentaerythrityl hexaheptanoate/hexacaprylate/hexacaprate, dipentaerythrityl hexahydroxystearate, disodium babassuamido MEA-sulfosuccinate, disodium cetyl phenyl ether disulfonate, disodium coceth-3 sulfosuccinate, disodium coco-glucoside citrate, disodium coco-glucoside sulfosuccinate, disodium decyl phenyl ether disulfonate, disodium laureth-7 citrate, disodium lauroamphodiacetate lauroyl sarcosinate, disodium oleyl phosphate, disodium peg-8 glyceryl caprylate/caprate, disodium peg-8 ricinosuccinate, disodium sitostereth-14 sulfosuccinate, distearamidopropylmethylamine, dodecylhexadecyltrimonium chloride, dodoxynol-13, ethyl hydroxyethyl cellulose, ethylene dihydrogenated tallowamide, hydrolyzed ethylene/MA copolymer, ethylhexyl coco-oleate estolide, ethylhexyl linoleoyl stearate, ethylhexylglyceryl behenate, ethylhexylglyceryl palmitate, ethylhexyloxyglyceryl palmitate, fluoro C2-8 alkyldimethicone, perfluorononylethyl carboxydecyl peg-10 dimethicone, fusel wheat bran/straw glycosides, glycereth-5 cocoate, glycereth-5 lactate, glycereth-6 laurate, glycereth-8 hydroxystearate, glycereth-20 stearate, glycereth-17 cocoate, glycereth-17 tallowate, glycereth-25 PCA isostearate, glyceryl arachidate, glyceryl arachidonate, glyceryl behenate, glyceryl behenate/eicosadioate, glyceryl capryl ether, glyceryl caprylate, glyceryl caprylate/caprate, glyceryl citrate/lactate/linoleate/oleate, glyceryl cocoate, glyceryl dilaurate, glyceryl dipalmitate, glyceryl erucate, glyceryl glycyrrhetinate, glyceryl hydrogenated sorbitan rapeseedate, glyceryl hydroxystearate, glyceryl isopalmitate, glyceryl isostearate, glyceryl isostearates, glyceryl isotridecanoate/stearate/adipate, glyceryl laurate, 1-glyceryl laurate, glyceryl laurate SE, glyceryl lauryl ether, glyceryl linoleate, (S)-glyceryl linoleate, glyceryl montanate, glyceryl myristate, glyceryl oleate citrate, glyceryl oleate SE, glyceryl oleate/elaidate, glyceryl palmitate lactate, glyceryl palmitoleate, glyceryl pentadecanoate, glyceryl ricinoleate SE, glyceryl sesquioleate, glyceryl stearate citrate, glyceryl stearate lactate, glyceryl stearate SE, glyceryl stearate/maleate, glyceryl tallowate, glyceryl undecylenate, glyceryl/sorbitol oleate/hydroxystearate, glycol cetearate, glycol ethylhexanoate, hexacosyl glycol isostearate, 2-hexyl decanoic acid, hexyldeceth-2, hexyldeceth-20, hydroxycetyl isostearate, hydroxycetyl phosphate, hydroxyethyldiethonium polyisobutenyl triethylaminosuccinate, hydroxypropylcocoate peg-8 dimethicone, hydroxystearyl alcohol, hydroxystearyl glucoside, hydroxysuccinimidyl C10-40 isoalkyl acidate, laneth-4 phosphate, laneth-5, laneth-10, laneth-10 acetate, laneth-16, hydrogenated laneth-20, laneth-25, hydrogenated laneth-25, laneth-50, laneth-75, lard glyceride, hydrogenated lard glyceride, laurdimonium chlorohydroxypropyl chloride, laurdimoniumhydroxypropyl cocoglucosides chloride, laurdimoniumhydroxypropyl decylglucosides chloride, laurdimoniumhydroxypropyl laurylglucosides chloride, laureth-1, laureth-2, laureth-3, isolaureth-3, laureth-3 carboxylic acid, laureth-4, laureth-4 phosphate, isolaureth-4 phosphate, laureth-5, laureth-5 butyl ether, laureth-5 carboxylic acid, laureth-6, isolaureth-6, laureth-7, laureth-7 phosphate, laureth-8, laureth-9, laureth-10, isolaureth-10, laureth-11, laureth-12, laureth-13, laureth-14, laureth-15, laureth-16, laureth-20, laureth-23, laureth-25, laureth-30, laureth-13 pg-hydroxyethylcellulose, laurimino bispropanediol, lauroyl ethyl glucoside, lauryl dimethicone peg-10 phosphate, lauryl dimethicone peg-15 crosspolymer, lauryl isopentyl-peg/ppg-18/18 methicone, lauryl peg-10 tris(trimethylsiloxy)silylethyl dimethicone, lauryl peg-8 ppg-8 dimethicone, lauryl phosphate, lauryl polyglyceryl-6 cetearyl glycol ether, lauryl sucrose, lauryl/myristyl wheat bran/straw glycosides, lecithin, hydroxylated lecithin, linseed acid, linseed oil polyglyceryl-4 esters, lithium myristate, lysolecithin, hydrogenated lysolecithin, hydrogenated lysophosphatidylcholine, lysophosphatidylglycerol, magnesium coceth sulfate, mannitan laurate, mannitan oleate, mannosylerythritol lipid, *Mauritia flexuosa* seed oil peg-8 esters, *Mauritia flexuosa* seed oil polyglyceryl-6 esters, MEA-laureth-6 carboxylate, MEA-ppg-8-steareth-7 carboxylate, hydrogenated menhaden acid, methoxy peg-17/dodecyl glycol copolymer, bismethoxy peg-40 polyepsilon caprolactone, methoxy peg/ppg-25/4 dimethicone, methyl gluceth-10, methyl glucose isostearate, methyl glucose laurate, methyl glucose sesquicaprylate/sesquicaprate, methyl glucose sesquicocoate, methyl glucose sesquiisostearate, methyl glucose sesquilaurate, methyl glucose sesquioleate, methyl glucose sesquistearate, methyl isostearate, methyl silanol peg-7 glyceryl cocoate, methyl silanol tri-peg-8 glyceryl cocoate, methylglucose dioleate/hydroxystearate, minkamidopropyl dimethylamine, myreth-2, myreth-3, myreth-4, myreth-5, isomyreth-9, myreth-10, isomyreth-3, myristoyl ethyl glucoside, myristoyl lactylic acid, myristyldimoniumhydroxypropyl cocoglucosides chloride, nonyl nonoxynol-5, oatamidopropyl dimethylamine, octadecenedioic acid, octyldecyl oleate, octyldecyl phosphate, octyldodeceth-2, octyldodeceth-5, octyldodeceth-10, octyldodeceth-16, octyldodeceth-20, octyldodeceth-25, octyldodecyl glucoside, octyldodecyl xyloside, oleamide DIPA, (Z)-oleic acid, oleoyl ethyl glucoside, oleth-10, oleth-11, oleth-12, oleth-15, oleth-16, oleth-45, oleth-2, oleth-2 phosphate, oleth-20 phosphate, oleth-3, oleth-30, oleth-35, oleth-4, oleth-40, oleth-5, oleth-6, oleth-7, oleth-8, oleth-82, oleth-9, oleyl phosphate, olivamidopropyltrimonium chloride, olive glycerides, olive oil glycereth-8 esters, olive oil peg-7 esters, olive oil peg-8 esters, olive oil peg-10 esters, olive oil peg/ppg-3/1 esters, olive oil polyglyceryl-6 esters, olive oil polyglyceryl-6 esters, palm acid, palm glyceride, hydrogenated palm glycerides, hydrogenated palm glycerides, palm kernel acid, palm kernel alcohol, palm kernel glycerides, acetylated palm kernel glycerides, palm kernel oil polyglyceryl-4 esters, palm kernelamide MIPA, hydrogenated palm oil, palm oil glycereth-8 esters, palm oil peg-8 esters, palm oil polyglyceryl-3 esters, palm oil polyglyceryl-4 esters, palm oil polyglyceryl-6 esters, hydrogenated palm/palm kernel glycerides, hydrogenated palm/palm kernel oil peg-6 esters, palmamide DEA, palmamide MEA, palmamide MIPA, palmeth-2, palmeth-2 phosphate, palmitamidobutyl guanidine acetate, palmitic acid, palmitoyl ethyltrimonium methosulfate, palmitoyl inulin, parinari curatellifolia oil peg-8 esters, parinari curatellifolia oil polyglyceryl-6 esters, peanut glycerides, peanutamide MIPA, peg-2 caprylylamine, peg-2 cocamide, peg-2 cocamine, peg-2 diisostearate, peg-2 dioleate, peg-2 hydrogenated castor oil, peg-2 hydrogenated tallow amine, peg-2 isostearate, peg-2 laurramide, peg-2 oleate SE, peg-2 olive glycerides, peg-2 sorbitan isostearate, peg-2 sorbitan trioleate, peg-2 soyamine, peg-2 stearate SE, peg-2 sunflower glycerides, peg-2 tallowamide DEA, peg-3 butylene glycol laurate, peg-3 castor oil, peg-3 cocamide DEA, peg-3 cocamine, peg-3 dicaprylate/caprate, peg-3 diisostearate, peg-3 distearate, peg-3 glyceryl cocoate, peg-3 glyceryl isostearate, peg-3 glyceryl triisostearate, peg-3 glyceryl trioleate, peg-3 glyceryl tristearate, peg-3 isostearate, peg-3 lanolate, peg-3 lauramide, peg-3 oleamide, peg-3 oleate, peg-3 sorbitan oleate, peg-3 sorbitan stearate, peg-3 sorbitan tristearate, peg-3 stearate, peg-3 tallow aminopropylamine, peg-3/ppg-2 glyceryl/sorbitol hydroxystearate/isostearate, peg-4 caprylic/capric glycerides, peg-4 castor oil, peg-4 cocamide, peg-4 cocamine, peg-4 diisostearate, peg-4 ethylhexanoate, peg-4 glyceryl tristearate, peg-4 isostearate, peg-4 lanolate, peg-4 oleate, peg-4 polyglyceryl-2 distearate, peg-4 polyglyceryl-2 stearate, peg-4 sorbitan stearate, peg-4 sorbitan triisostearate, peg-4 stearate, peg-4 tallate, peg-4 trimethylolpropane distearate, peg-5 castor oil, peg-5 cocamine, peg-5 glyceryl isostearate, peg-5 glyceryl oleate, peg-5 glyceryl stearate, peg-5 glyceryl triisostearate, peg-5 glyceryl trioleate, peg-5 glyceryl tristearate, peg-5 hydrogenated castor oil, peg-5 hydrogenated castor oil isostearate, peg-5 hydrogenated castor oil triisostearate, peg-5 hydrogenated corn glycerides, peg-5 hydrogenated lanolin, peg-5 lanolate, peg-5 lanolin, peg-5 lanolinamide, peg-5 lauramide, peg-5 oleamide dioleate, peg-5 oleamine, peg-5 oleate, peg-5 phytosterol, peg-5 rapeseed sterol, peg-5 soy sterol, peg-5 soyamine, peg-5 stearamine, peg-5 stearate, peg-5 tallate, peg-5 tricapryl citrate, peg-5 trimethylolpropane trimyristate, peg-5 tsubakiate glycerides, peg-6 almond glycerides, peg-6 beeswax, peg-6 butylene glycol laurate, peg-6 caprylate/caprate, peg-6 diisostearate, peg-6 dioleate, peg-6 glyceryl caprate, peg-6 glyceryl isostearate, peg-6 glyceryl tristearate, peg-6 hydrogenated castor oil, peg-6 hydrogenated palm/palm kernel glyceride, peg-6 hydrogenated palmamide, peg-6 isopalmitate, peg-6 isostearate, peg-6 lanolate, peg-6 lauramide, peg-6 laurate, peg-6 laurate/tartrate, peg-6 methicone acetate, peg-6 methyl ether dimethicone, peg-6 oleamine, peg-6 oleate, peg-6 olive glycerides, peg-6 propylene glycol caprylate/caprate, peg-6 sorbitan oleate, peg-6 sorbitan stearate, peg-6 stearate, peg-6 stearylguanidine, peg-7 caprylic/capric glycerides, peg-7 cocamide, peg-7 cocoglycerides, peg-7 glyceryl soyate, peg-7 hydrogenated castor oil, peg-7 lanolate, peg-7 methyl ether dimethicone, peg-7 oleate, peg-7 olive glycerides, peg-7 ricinoleamide, peg-7 sunflower glycerides, peg-7 tallow amine, peg-7 trimethylolpropane coconut ether, peg-8 avocadoate, peg-8 behenate, peg-8 C12-18 alkyl ester, peg-8 caprate, peg-8 caprylate, peg-8 caprylate/caprate, peg-8 caprylic/capric glycerides, peg-8 castor oil, peg-8 cocamine, peg-8 cranberriate, peg-8 di/triricinoleate, peg-8 dicocoate, peg-8 diisostearate, peg-8 dodecenylsuccinate, peg-8 glyceryl isostearate, peg-8 hydrogenated castor oil, peg-8 hydrogenated fish glycerides, peg-8 isostearate, peg-8 lanolate, peg-8 myristate, peg-8 oleate, peg-8 peg-4 dimethicone, peg-8 raspberriate, peg-8 sesquilaurate, peg-8 sesquioleate, peg-8 soyamine, peg-8 tallate, peg-8 trisiloxane, peg-8 undecylenate, peg-9 avocadoate, peg-9 borageate, peg-9 butylene glycol laurate, peg-9 butyloctanoate, peg-9 castor oil, peg-9 cocoglycerides, peg-9 diethylmonium chloride, peg-9 glyceryl isostearate, peg-9 grapeseedate, peg-9 isostearate, peg-9 laurate, peg-9 methyl ether dimethicone, peg-9 octyldodecanoate, peg-9 oleate, peg-9 polydimethylsiloxyethyl dimethicone, peg-9 soyate, peg-9 stearate, peg-10 butylene glycol isostearate, peg-10 castor oil, peg-10 cocamine, peg-10 cocoate, peg-10 dioleate, peg-10 glyceryl diisostearate, peg-10 glyceryl isostearate, peg-10 glyceryl oleate, peg-10 glyceryl stearate, peg-10 glyceryl triisostearate, peg-10 glyceryl trioleate, peg-10 glyceryl tristearate, peg-10 hydrogenated castor oil, peg-10 hydrogenated castor oil isostearate, peg-10 hydrogenated castor oil triisostearate, peg-10 hydrogenated lanolin, peg-10 hydrogenated tallow amine, peg-10 isolauryl thioether, peg-10 isostearate, peg-10 lanolate, peg-10 lanolin, peg-10 laurate, peg-10 methyl ether dimethicone, peg-10 oleamine, peg-10 oleate, peg-10 olive glycerides, peg-10 phytosterol, peg-10 rapeseed sterol, peg-10 sorbitan laurate, peg-10 soy sterol, peg-10 soyamine, peg-10 stearamide, peg-10 stearate, peg-10 sunflower glycerides, peg-10 tallate, peg-10 tallow aminopropyl amine, peg-10 tsubakiate glycerides, peg-11 avocado glycerides, peg-11 babassu glycerides, peg-11 castor oil, peg-11 cocamide, peg-11 cocoa butter glycerides, peg-11 lauramide, peg-11 methyl ether dimethicone, peg-11 oleate, peg-11 tallow amine, peg-12 beeswax, peg-12 cocamine, peg-12 diisostearate, peg-12 dilaurate, peg-12 dimethicone crosspolymer, peg-12 dioleate, peg-12 distearate, peg-12 ditallate, peg-12 glyceryl laurate, peg-12 isostearate, peg-12 lanolate, peg-12 laurate, peg-12 oleate, peg-12 palm kernel glycerides, peg-12 stearate, peg-12 tallate, peg-13 diphenylol propane, peg-13 ethylhexanoate, peg-13 hydrogenated tallow amide, peg-13 sunflower glycerides, peg-14 avocado glycerides, peg-14 laurate, peg-14 oleate, peg-14 stearate, peg-14 tallate, peg-15 butanediol, peg-15 butylene glycol diisostearate, peg-15 castor oil, peg-15 cocamine, peg-15 cocamine oleate/phosphate, peg-15 cocoate, peg-15 cocopolyamine, peg-15 glyceryl diisostearate, peg-15 glyceryl laurate, peg-15 glyceryl oleate, peg-15 glyceryl ricinoleate, peg-15 glyceryl stearate, peg-15 glyceryl triisostearate, peg-15 glyceryl trioleate, peg-15 glyceryl tristearate, peg-15 hydrogenated castor oil isostearate, peg-15 hydrogenated castor oil triisostearate, peg-15 hydrogenated lanolin, peg-15 hydrogenated tallow amine, peg-15 hydroxystearate, peg-15 jojoba acid, peg-15 jojoba alcohol, peg-15 lanolate, bis-peg-15 methyl ether dimethicone, peg-15 oleamine, peg-15 oleate, peg-15 phytosterol, peg-15 soyamine, peg-15 stearamide, peg-15 stearamine, peg-15 stearate, peg-15 tallate, peg-15 tallow aminopropyl amine, peg-16 castor oil, peg-16 cetyl/oleyl/stearyl/lanolin alcohol ether, peg-16 dilaurate, peg-16 hydrogenated castor oil, peg-16 macadamia glycerides, peg-16 oleate, peg-16 soy sterol, peg-16 tallate, peg-18 castor oil dioleate, peg-18 glyceryl oleate/cocoate, peg-18 palm glycerides, peg-18 stearate, peg-20 almond glycerides, peg-20 beeswax, peg-20 castor oil, peg-20 cocamide, peg-20 cocamine, peg-20 corn glycerides, peg-20 dioleate, peg-20 evening primrose glycerides, peg-20 glyceryl diisostearate, peg-20 glyceryl triisostearate, peg-20 glyceryl trioleate, peg-20 glyceryl tristearate, peg-20 hexadecenylsuccinate, peg-20 hydrogenated castor oil, peg-20 hydrogenated castor oil isostearate, peg-20 hydrogenated castor oil PCA isostearate, peg-20 hydrogenated dimer dilinoleate, peg-20 hydrogenated palm glycerides, peg-20 isostearate, peg-20 lanolate, peg-20 lanolin, peg-20 mannitan laurate, peg-20 methyl glucose sesquicaprylate/sesquicaprate, peg-20 methyl glucose sesquilaurate, peg-20 myristate, peg-20 oleamine, peg-20 oleate, peg-20 sorbitan isostearate, peg-20 sorbitan oleate, peg-20 sorbitan triisostearate, peg-20 soy sterol, peg-20 tallate, peg-20 tsubakiate glycerides, peg-20-ppg-10 glyceryl stearate, peg-23 hexadecyleicosanoate, peg-23 octyldodecanoate, peg-23 oleate, peg-23 stearate, peg-24 hydrogenated lanolin, peg-24 lanolin, peg-25 butylene glycol isostearate, peg-25 glyceryl isostearate, peg-25 glyceryl trioleate, peg-25 hydrogenated castor oil, peg-25 moringa glycerides, peg-25 phytostanol, peg-25 propylene glycol stearate, peg-25 soy sterol, peg-25 stearate, peg-26 castor oil, peg-26 jojoba acid, peg-26 jojoba alcohol, peg-27 lanolin, peg-30 castor oil, peg-30 glyceryl diisostearate, peg-30 glyceryl triisostearate, peg-30 glyceryl trioleate, peg-30 hydrogenated castor oil, peg-30 hydrogenated castor oil isostearate, peg-30 hydrogenated castor oil PCA isostearate, peg-30 hydrogenated castor oil triisostearate, peg-30 hydrogenated dimer dilinoleate, peg-30 hydrogenated lanolin, peg-30 isostearate, peg-30 lanolin, peg-30 oleamine, peg-30 phytosterol, peg-30 sorbitan tetraoleate, peg-30 soy sterol, peg-32 dioleate, peg-32 methyl ether dimethicone, peg-32 oleate, peg-32 stearate, peg-33 castor oil, peg-35 almond glycerides, peg-35 hydrogenated castor oil, peg-35 lanolin, peg-35 soy glycerides, peg-35 stearate, peg-36 castor oil, peg-36 oleate, peg-36 stearate, peg-40 distearate, peg-40 glyceryl isostearate, peg-40 glyceryl stearate, peg-40 glyceryl triisostearate, peg-40 glyceryl trioleate, peg-40 hydrogenated castor oil isostearate, peg-40 hydrogenated castor oil triisostearate, peg-40 hydrogenated dimer dilinoleate, peg-40 hydrogenated lanolin, peg-40 isostearate, peg-40 jojoba acid, peg-40 jojoba alcohol, peg-40 lanolin, peg-40 olive glycerides, peg-40 ricinoleamide, peg-40 sorbitan diisostearate, peg-40 sorbitan laurate, peg-40 sorbitan oleate, peg-40 sorbitan perisostearate, peg-40 sorbitan stearate, peg-40 sorbitan tetraoleate, peg-40 soy sterol, peg-42 babassu glycerides, peg-42 mushroom glycerides, peg-44 castor oil, peg-45 hydrogenated castor oil, peg-45 palm kernel glycerides, peg-45 safflower glycerides, peg-45 stearate, peg-50 castor oil, peg-50 glyceryl isostearate, peg-50 glyceryl triisostearate, peg-50 glyceryl trioleate, peg-50 hydrogenated castor oil isostearate, peg-50 hydrogenated castor oil succinate, peg-50 hydrogenated castor oil triisostearate, peg-50 lanolin, peg-50 stearamide, peg-50 stearamine, peg-54 castor oil, peg-54 hydrogenated castor oil, peg-55 castor oil, peg-55 hydrogenated castor oil, peg-55 lanolin, peg-55 stearate, peg-58 hydrogenated castor oil isostearate, peg-60 castor oil, peg-60 castor oil isostearate, peg-60 corn glycerides, peg-60 evening primrose glycerides, peg-60 glyceryl diisostearate, peg-60 glyceryl stearate, peg-60 glyceryl triisostearate, peg-60 glyceryl trioleate, peg-60 hydrogenated castor oil, peg-60 hydrogenated castor oil triisostearate, peg-60 hydrogenated dimer dilinoleate, peg-60 lanolin, peg-60 *Passiflora edulis* seed glycerides, peg-60 *Passiflora incarnata* seed glycerides, peg-60 shea butter glycerides, peg-60 sorbitan tetraoleate, peg-60 sorbitan tetrastearate, peg-60 tsubakiate glycerides, peg-65 butylene glycol isostearate, peg-65 hydrogenated castor oil, peg-66 trihydroxystearin, peg-70 hydrogenated lanolin, peg-70 mango glycerides, peg-75 beta-sitosterol, peg-75 castor oil, peg-75 cocoa butter glycerides, peg-75 *Crambe abyssinica* seed oil, peg-75 dioleate, peg-75 lanolin, peg-75 lanolin wax, peg-75 meadowfoam oil, peg-75 propylene glycol stearate, peg-75 shea butter glycerides, peg-75 shorea butter glycerides, peg-75 soy glycerides, peg-80 castor oil, peg-80 hydrogenated castor oil, peg-80 hydrogenated dimer dilinoleate, peg-80 hydrogenated glyceryl palmate, peg-80 methyl glucose laurate, peg-80 sorbitan palmitate, peg-82 glyceryl tallowate, peg-85 lanolin, peg-90/polyepsilon caprolactone, peg-100 castor oil, peg-100 hydrogenated castor oil, peg-100 lanolin, peg-114 polylactic acid, peg-12 glyceryl dioleate, peg-12 palmitamine, peg-120 distearate, peg-120 methyl glucose dioleate, peg-120 propylene glycol stearate, peg-130 glyceryl tallowate, peg-140 glyceryl tristearate, peg-15 cocomonium chloride, peg-15 glyceryl isostearate, peg-15 tallow polyamine, peg-150 dibehenate, peg-150 dilaurate, peg-150 dioleate, peg-150 lanolin, peg-150 polyglyceryl-2 tristearate, peg-160 sorbitan triisostearate, peg-175 diisostearate, peg-175 distearate, peg-18 palmitate, peg-190 distearate, peg-192 apricot kernel glycerides, peg-2 castor oil, peg-2 cocomonium chloride, peg-2 diethylhexanoate, peg-2 dilaurate, peg-2 distearate, peg-2 laurate SE, peg-2 oleamine, peg-2 oleammonium chloride, peg-2 ricinoleate, peg-2 stearmonium chloride, peg-20 cocamide MEA, peg-20 dilaurate, peg-20 distearate, peg-20 glyceryl laurate, peg-20 glyceryl oleate, peg-20 glyceryl ricinoleate, peg-20 glyceryl stearate, peg-20 hydrogenated lanolin, peg-20 laurate, peg-20 methyl glucose distearate, peg-20 methyl glucose sesquistearate, peg-20 palmitate, peg-20 phytosterol, peg-20 sorbitan cocoate, peg-20 stearate, peg-20 tallowate, peg-200 castor oil, peg-200 glyceryl tallowate, peg-200 hydrogenated castor oil, peg-200 hydrogenated glyceryl palmate, peg-200 trihydroxystearin, peg-22/dodecyl glycol copolymer, peg-23 glyceryl laurate, peg-23 olivate, peg-25 castor oil, peg-25 glyceryl oleate, peg-25 glyceryl stearate, peg-28 glyceryl tallowate, peg-29 castor oil, peg-3 cocamide, peg-3 dioleate, peg-3 dipalmitate, peg-30 dipolyhydroxystearate, peg-30 glyceryl cocoate, peg-30 glyceryl laurate, peg-30 glyceryl oleate, peg-30 glyceryl stearate, peg-30 hydrogenated tallow amine, peg-30 stearate, peg-32 dilaurate, peg-32 distearate, peg-35 castor oil, peg-4 dicocoate, peg-4 diheptanoate, peg-4 dioleate, peg-4 distearate, peg-4 laurate, peg-4 oleamide, peg-4 olivate, peg-40 castor oil, peg-40 glyceryl cocoate, peg-40 hydrogenated castor oil, peg-40 hydrogenated tallow amine, peg-40 sorbitan lanolate, peg-40 sorbitan peroleate, peg-40 stearate, peg-5 cocamide, peg-5 cocoate, peg-5 ethylhexanoate, peg-5 glyceryl sesquioleate, peg-5 hydrogenated tallow amine, peg-5 isononanoate, peg-5 oleamide, peg-5 sorbitan isostearate, peg-5 tallow amide, peg-50 hydrogenated tallow amine, peg-50 shea butter, peg-50 stearate, peg-50 tallow amide, peg-6 caprylic/capric glycerides, peg-6 dilaurate, peg-6 distearate, peg-6 isolauryl thioether, peg-6 oleamide, peg-6 palmitate, peg-60 almond glycerides, peg-7 glyceryl cocoate, peg-7 oleamide, peg-7 olivate, peg-7 ricinoleate, peg-7 stearate, peg-75 dilaurate, peg-75 distearate, peg-75 lanolin oil, peg-75 sorbitan lanolate, peg-78 glyceryl cocoate, peg-8 beeswax, peg-8 cocoate, peg-8 dilaurate, peg-8 dioleate, peg-8 distearate, peg-8 ditallate, peg-8 glyceryl laurate, peg-8 hydrogenated tallow amine, peg-8 isolauryl thioether, peg-8 laurate, peg-8 propylene glycol cocoate, peg-8 stearate, peg-8 tallow amide, peg-80 glyceryl cocoate, peg-80 glyceryl tallowate, peg-9 cocoate, peg-9 distearate, peg-9 oleamide, peg-9 oliveate, peg-9 stearamide carboxylic acid, peg/poly (1,2-butanediol)-52/32 dimethyl ether, peg/ppg-2/16 copolymer, peg/ppg-3/30 copolymer, peg/ppg-5/21 copolymer, peg/ppg-6/39 copolymer, peg/ppg-6/67 copolymer, peg/ppg-7/21 copolymer, peg/ppg-7/22 copolymer, peg/ppg-7/91 copolymer, peg/ppg-8/30 copolymer, peg/ppg-8/35 copolymer, peg/ppg-10/2 copolymer, peg/ppg-10/30 copolymer, peg/ppg-10/47 copolymer, peg/ppg-11/16 copolymer, peg/ppg-11/21 copolymer, peg/ppg-12/136 copolymer, peg/ppg-12/23 copolymer, peg/ppg-12/4 copolymer, peg/ppg-12/9 copolymer, peg/ppg-13/30 copolymer, peg/ppg-13/67 copolymer, peg/ppg-18/14 copolymer, peg/ppg-18/163 copolymer, peg/ppg-18/34 copolymer, peg/ppg-18/51 copolymer, peg/ppg-19/30 copolymer, peg/ppg-20/54 copolymer, peg/ppg-21/15 copolymer, peg/ppg-21/39 copolymer, peg/ppg-21/47 copolymer, peg/ppg-21/67 copolymer, peg/ppg-21/7 copolymer, peg/ppg-22/39 copolymer, peg/ppg-24/35 copolymer, peg/ppg-30/160 copolymer, peg/ppg-31/54 copolymer, peg/ppg-38/54 copolymer, peg/ppg-46/16 copolymer, peg/ppg-52/35 copolymer, peg/ppg-62/39 copolymer, peg/ppg-97/39 copolymer, peg/ppg-98/67 copolymer, peg/ppg-10/2 diricinoleate, peg/ppg-10/2 propylheptyl ether, peg/ppg-10/3 oleyl ether dimethicone, peg/ppg-12/16 dimethicone, peg/ppg-12/18 dimethicone, peg/ppg-122/47 copolymer, peg/ppg-128/54 copolymer, bis-peg/ppg-14/14 dimethicone, peg/ppg-14/2 propylheptyl ether, peg/ppg-14/4 dimethicone, peg/ppg-15/15 acetate dimethicone, peg/ppg-15/15 allyl ether acetate, peg/ppg-15/5 dimethicone, peg/ppg-150/30 copolymer, bis-peg/ppg-16/16 peg/ppg-16/16 dimethicone, peg/ppg-16/2 dimethicone, peg/ppg-16/8 dimethicone, peg/ppg-17/18 dimethicone, peg/ppg-18/18 dimethicone, peg/ppg-18/18 isostearate, peg/ppg-18/18 laurate, peg/ppg-18/6 copolymer, bis-peg/ppg-18/6 dimethicone, peg/ppg-19/19 dimethicone, peg/ppg-20/15 dimethicone, peg/ppg-20/20 dimethicone, bis-peg/ppg-20/20 dimethicone, peg/ppg-20/22 methyl ether dimethicone, peg/ppg-20/29 dimethicone, bis-peg/ppg-20/5 peg/ppg-20/5 dimethicone, peg/ppg-20/6 dimethicone, peg/ppg-22/22 butyl ether dimethicone, peg/ppg-22/23 butyl ether dimethicone, peg/ppg-22/23 dimethicone, peg/ppg-22/24 dimethicone, peg/ppg-23/23 butyl ether dimethicone, peg/ppg-24/18 butyl ether dimethicone, peg/ppg-25/25 dimethicone, peg/ppg-27/27 dimethicone, peg/ppg-27/9 butyl ether dimethicone, peg/ppg-3/10 dimethicone, peg/ppg-30/10 dimethicone, peg/ppg-32/3 diricinoleate, peg/ppg-4/12 dimethicone, peg/ppg-4/2 propylheptyl ether, peg/ppg-40/2 propylheptyl ether, peg/ppg-5/3 trisiloxane, peg/ppg-6/11 dimethicone, peg/ppg-6/2 glyceryl cocoate, peg/ppg-6/2 propylheptyl ether, peg/ppg-7/2 propylheptyl ether, peg/ppg-8/13 diisostearate, peg/ppg-8/14 dimethicone, peg/ppg-8/2 propylheptyl ether, peg/ppg-8/3 diisostearate, peg/ppg-8/3 laurate, pentaerythrityl distearate, pentaerythrityl tetraisostearate, neopentyl glycol diisostearate, neopentyl glycol dilaurate, hydrogenated phosphatidylcholine, phosphatidylcholine, egg yolk, phosphatidylglycerol, *Pinus sibirica* seed oil polyglyceryl-6 esters, poloxamer 105 benzoate, poloxamer 182 dibenzoate, poloxamine 1101, poloxamine 1102, poloxamine 1104, poloxamine 1301, poloxamine 1302, poloxamine 1304, poloxamine 1307, poloxamine 1501, poloxamine 1502, poloxamine 1508, poloxamine 304, poloxamine 504, poloxamine 604, poloxamine 701, poloxamine 702, poloxamine 704, poloxamine 707, poloxamine 901, poloxamine 904, poloxamine 908, poly(C6-14 olefin), polyacrylate-29, polyester-6, polyglyceryl dimer soyate, polyglyceryl-2 oleate, polyglyceryl-2 stearate, polyglyceryl-4 oleate, polyglyceryl-4 pentastearate, polyglyceryl-4 stearate, polyglyceryl-6 caprylate, polyglyceryl-6 distearate, polyglyceryl-6 laurate, polyglyceryl-6 myristate, polyglyceryl-6 octastearate, polyglyceryl-6 oleate, polyglyceryl-6 pentastearate, polyglyceryl-6 polyricinoleate, polyglyceryl-6 tristearate, polyglyceryl-8 oleate, polyglyceryl-8 stearate, polyglyceryl-10 decamacadamiate, polyglyceryl-10 diisostearate, polyglyceryl-10 dioleate, polyglyceryl-10 distearate, polyglyceryl-10 pentaisostearate, polyglyceryl-10 pentaoleate, polyglyceryl-10 apricot kernelate, polyglyceryl-10 behenate/eicosadioate, polyglyceryl-10 bis(hydroxypropyl lauryl ether), polyglyceryl-10 caprate, polyglyceryl-10 caprylate, polyglyceryl-10 cocoate, polyglyceryl-10 decahydroxystearate, polyglyceryl-10 decalinoleate, polyglyceryl-10 dicocoate, polyglyceryl-10 didecanoate, polyglyceryl-10 dimyristate, polyglyceryl-10 dipalmitate, polyglyceryl-10 dodecabehenate, polyglyceryl-10 dodecacaprate, polyglyceryl-10 dodecacaprylate, polyglyceryl-10 hepta(behenate/stearate), polyglyceryl-10 hexaerucate, polyglyceryl-10 hexaisostearate, polyglyceryl-10 hexaoleate, polyglyceryl-10 hydroxypropyl ethylhexyl ether, polyglyceryl-10 hydroxypropyl lauryl ether, polyglyceryl-10 lauryl ether, polyglyceryl-10 palmate, polyglyceryl-10 pentacaprylate, polyglyceryl-10 pentalaurate, polyglyceryl-10 pentalinoleate, polyglyceryl-10 pentaricinoleate, polyglyceryl-10 polyhydroxystearate, polyglyceryl-10 sesquistearate, polyglyceryl-10 tricocoate, polyglyceryl-10 tridecanoate, polyglyceryl-12 bis(hydroxypropyl ethylhexyl ether), polyglyceryl-2 caprate, polyglyceryl-2 caprylate, polyglyceryl-2 diisostearate, polyglyceryl-2 distearate, polyglyceryl-2 hydroxypropyl ethylhexyl ether, polyglyceryl-2 hydroxypropyl lauryl ether, polyglyceryl-2 isononanoate/dimer dilinoleate copolymer, polyglyceryl-2 isopalmitate, polyglyceryl-2 isopalmitate/sebacate, polyglyceryl-2 lanolin alcohol ether, polyglyceryl-2 laurate, polyglyceryl-2 lauryl ether, polyglyceryl-2 myristate, polyglyceryl-2 oleyl ether, polyglyceryl-2 palmitate, polyglyceryl-2 sesquicaprylate, polyglyceryl-2 sesquioleate, polyglyceryl-2 sesquistearate, polyglyceryl-2 sorbitan tetraethylhexanoate, polyglyceryl-2 tetraoleate, polyglyceryl-2 tetrastearate, polyglyceryl-2-peg-4 stearate, polyglyceryl-20 docosabehenate/isostearate, polyglyceryl-20 docosabehenate/laurate, polyglyceryl-20 docosabehenate/oleate, polyglyceryl-20 heptadecabehenate/laurate, polyglyceryl-20 octadecabehenate/laurate, polyglyceryl-20 octaisononanoate, polyglyceryl-3 beeswax, polyglyceryl-3 caprate, polyglyceryl-3 caprylate, polyglyceryl-3 cetyl ether, polyglyceryl-3 cetyl ether stearate, polyglyceryl-3 cocoate, polyglyceryl-3 decyltetradecyl ether, polyglyceryl-3 dicaprate, polyglyceryl-3 dicitrate/stearate, polyglyceryl-3 dicocoate, polyglyceryl-3 dihydroxy stearate, polyglyceryl-3 dihydroxystearate, isopolyglyceryl-3 dimethicone, isopolyglyceryl-3 dimethiconol, polyglyceryl-3 dioleate, polyglyceryl-3 distearate, polyglyceryl-3 hydroxylauryl ether, polyglyceryl-3 hydroxypropyl ethylhexyl ether, polyglyceryl-3 hydroxypropyl lauryl ether, polyglyceryl-3 isostearate, polyglyceryl-3 laurate, polyglyceryl-3 methylglucose distearate, polyglyceryl-3 myristate, polyglyceryl-3 oleyl ether phosphate, polyglyceryl-3 palmitate, polyglyceryl-3 pentaricinoleate, polyglyceryl-3 polyricinoleate, polyglyceryl-3 rice branate, polyglyceryl-3 rice branate phosphate, polyglyceryl-3 ricinoleate, polyglyceryl-3 sorbityl linseedate, polyglyceryl-3 soyate/shea butterate, polyglyceryl-3 stearate, polyglyceryl-3 stearate SE, polyglyceryl-3 triisostearate, polyglyceryl-4 almondate/shea butterate, polyglyceryl-4 caprate, polyglyceryl-4 caprylate, polyglyceryl-4 cocoate, polyglyceryl-4 diisostearate/polyhydroxystearate/sebacate, polyglyceryl-4 dilaurate, polyglyceryl-4 distearate, polyglyceryl-4 hazelseedate, polyglyceryl-4 hydroxypropyl ethylhexyl ether, polyglyceryl-4 isostearate, polyglyceryl-4 isostearate/laurate, polyglyceryl-4 laurate, polyglyceryl-4 lauryl ether, polyglyceryl-4 oleyl ether, polyglyceryl-4 pentaoleate, polyglyceryl-4 pentapalmitate/stearate, polyglyceryl-4 polyricinoleate, polyglyceryl-4 sorbityl ether olivate phosphate, polyglyceryl-4 sweet almondate, polyglyceryl-4 tristearate, polyglyceryl-4-peg-2 cocamide, polyglyceryl-5 bis(hydroxypropyl ethylhexyl ether), polyglyceryl-5 caprate, polyglyceryl-5 dilaurate, polyglyceryl-5 dioleate, polyglyceryl-5 hexastearate, polyglyceryl-5 hydroxypropyl lauryl ether, polyglyceryl-5 isostearate, polyglyceryl-5 laurate, polyglyceryl-5 myristate, polyglyceryl-5 oleate, polyglyceryl-5 pentamyristate, polyglyceryl-5 polyricinoleate, polyglyceryl-5 stearate, polyglyceryl-5 tribehenate, polyglyceryl-5 triisostearate, polyglyceryl-5 trimyristate, polyglyceryl-5 trioleate, polyglyceryl-5 tristearate, polyglyceryl-6 *Aadansonia digitata* seedate, polyglyceryl-6 apricot kernelate, polyglyceryl-6 argan kernelate, polyglyceryl-6 bis(hydroxypropyl ethylhexyl ether), polyglyceryl-6 bis(hydroxypropyl lauryl ether), polyglyceryl-6 caprate, polyglyceryl-6 *Citrullus lanatus* seedate, polyglyceryl-6 dicaprate, polyglyceryl-6 diisostearate, polyglyceryl-6 dioleate, polyglyceryl-6 dipalmitate, polyglyceryl-6 heptacaprylate, polyglyceryl-6 hexaoleate, polyglyceryl-6 hexastearate, polyglyceryl-6 isostearate, polyglyceryl-6 myristyl ether, polyglyceryl-6 palmitate, polyglyceryl-6 palmitate/succinate, polyglyceryl-6 pentaoleate, polyglyceryl-6 pentaricinoleate, polyglyceryl-6 polyhydroxystearate, polyglyceryl-6 ricinoleate, polyglyceryl-6 sesquiisostearate, polyglyceryl-6 sesquistearate, polyglyceryl-6 tetrabehenate, polyglyceryl-6 tetraoleate, polyglyceryl-6 undecylenate, polyglyceryl-8 $C_{12-20}$ acid ester, polyhydroxystearic acid, polyperfluoroethoxymethoxy peg-2 phosphate, polyquaternium-75, polyquaternium-77, polyquaternium-78, polyquaternium-79, polyquaternium-80, polyquaternium-81, polyquaternium-88, polysorbate 20, polysorbate 21, polysorbate 40, polysorbate 60, polysorbate 61, polysorbate 65, polysorbate 80, polysorbate 80 acetate, polysorbate 85, polyurethane-28, potassium babassuate, potassium cocoate, potassium cocoyl rice amino acids, potassium cornate, potassium deceth-4 phosphate, potassium dextrin octenylsuccinate, potassium dimethicone peg-7 phosphate, potassium laurate, potassium laureth phosphate, potassium lauryl sulfate, potassium myristate, potassium octoxynol-12 phosphate, potassium oleate, potassium olivate, potassium palmitate, potassium peanutate, potassium peg-50 hydrogenated castor oil succinate, potassium stearate, potassium tallowate, potassium tsubakiate, potassium undecylenate, ppg-1 beheneth-15, ppg-1 hydroxyethyl caprylamide, ppg-1 trideceth-13, ppg-1-deceth-4, ppg-1-deceth-5, ppg-1-deceth-6, ppg-1-deceth-7, ppg-1-isodeceth-4, ppg-1-isodeceth-6, ppg-1-isodeceth-7, ppg-1-isodeceth-9, ppg-1-peg-9 lauryl glycol ether, ppg-2 $C_{12-13}$ pareth-8, ppg-2 $C_{12-15}$ pareth-6, ppg-2 C9-11 pareth-5, ppg-2 C9-11 pareth-7, ppg-2 C9-11 pareth-8, ppg-2 glyceryl ether, ppg-2 hydroxyethyl cocamide, ppg-2 isoceteth-20 acetate, ppg-2 lanolin alcohol ether, ppg-2-ceteareth-9, ppg-2-deceth-10, ppg-2-deceth-12, ppg-2-deceth-15, ppg-2-deceth-20, ppg-2-deceth-3, ppg-2-deceth-30, ppg-2-deceth-40, ppg-2-deceth-5, ppg-2-deceth-50, ppg-2-deceth-60, ppg-2-deceth-7, ppg-2-deceth-8, ppg-2-isodeceth-10, ppg-2-isodeceth-12, ppg-2-isodeceth-18, ppg-2-isodeceth-25, ppg-2-isodeceth-4, ppg-2-isodeceth-6, ppg-2-isodeceth-8, ppg-2-isodeceth-9, ppg-2-laureth-12, ppg-2-laureth-5, ppg-2-laureth-8, ppg-2-peg-11 hydrogenated lauryl alcohol ether, ppg-2-peg-6 coconut oil esters, ppg-2/peg-8 cocoate, ppg-3 $C_{12-14}$ sec-pareth-7, ppg-3 glyceryl ether, ppg-3 hydroxyethyl soyamide, ppg-3-deceth-2 carboxylic acid, ppg-3-isosteareth-9, ppg-3-laureth-10, ppg-3-laureth-12, ppg-3-laureth-8, ppg-3-laureth-9, ppg-3-myreth-11, ppg-3-myreth-3, ppg-3-peg-6 oleyl ether, ppg-4 $C_{12-14}$ sec pareth-7, ppg-4 $C_{12-14}$ sec-pareth-5, ppg-4 C13-15 pareth-15, ppg-4 laureth-7, ppg-4 trideceth-6, ppg-4-ceteareth-12, ppg-4-ceteth-10, ppg-4-ceteth-20, ppg-4-deceth-4, ppg-4-deceth-6, ppg-4-isodeceth-10, ppg-5 $C_{12-14}$ sec-pareth-7, ppg-5 $C_{12-14}$ sec-pareth-9, ppg-5 C9-15 pareth-6, ppg-5 phytosterol, ppg-5-ceteth-20, ppg-6 C12-18 pareth-11, ppg-6 glyceryl ether, ppg-6 trideceth-8, ppg-6-deceth-9, ppg-6-decyltetradeceth-12, ppg-6-decyltetradeceth-20, ppg-6-decyltetradeceth-30, bis-(ppg-7 undeceneth-21) dimethicone, ppg-7/peg-30 phytosterol, ppg-8 glyceryl ether, ppg-8 polyglyceryl-2 ether, ppg-8-ceteth-20, ppg-8-deceth-6, ppg-9 glyceryl ether, ppg-9-ethylhexeth-5, ppg-10 glyceryl ether, ppg-10 jojoba alcohol, ppg-10 lanolin alcohol ether, ppg-10-ceteareth-20, ppg-12 capryleth-18, ppg-12 diglucosyl C14-18 acidate, ppg-12-laneth-50, ppg-12-peg-65 lanolin oil, ppg-13 decyltetradeceth-24, ppg-14 diglyceryl ether, ppg-14 polyglyceryl-2 ether, ppg-14-deceth-6, ppg-16 glyceryl ether, ppg-20 lanolin alcohol ether, ppg-20-decyltetradeceth-10, ppg-21 butyl ether phosphate, ppg-23-peg-4 trimethylolpropane, ppg-23-steareth-34, ppg-25 butyl ether phosphate, ppg-25-glycereth-22, ppg-27 glyceryl ether, ppg-30 ethylhexeth-4 phosphate, ppg-30 lanolin alcohol ether, ppg-30 steareth-4, ppg-34 steareth-3, ppg-35 butyl ether phosphate, ppg-40-peg-60 lanolin oil, ppg-50 glyceryl ether, ppg-10 cetyl ether phosphate, ppg-12-peg-50 lanolin, ppg-24-glycereth-24, ppg-25-laureth-25, ppg-5-ceteth-10 phosphate, ppg-5-laureth-5, ppg-6 $C_{12-15}$ pareth-12, ppg-6 C9-11 pareth-5, ppg-6-deceth-4, ppg-66-glycereth-12, ppg-9 diethylmonium chloride, ppg/peg-2/10 glyceryl cocoate, isopropyl lanolate, isopropyl titanium triisostearate, propylene glycol capreth-4, propylene glycol dicocoate, propylene glycol hyaluronate, propylene glycol isodeceth-4, propylene glycol oleate SE, propylene glycol oleth-5, propylene glycol ricinoleate, propylene glycol stearate, propylene glycol stearate SE, pumpkin seed oil peg-8 esters, quaternium-90 montmorillonite, quaternium-92, *Quillaja saponaria* bark, *Quillaja saponaria* bark extract, raffinose myristate, raffinose oleate, rapeseed glucoside, rapeseed glyceride, hydrogenated rapeseed glycerides, rapeseed oil peg-3 esters, rapeseed oil peg-20 esters, rapeseed oil sorbitol esters, raspberry seed oil peg-8 esters, rhamnolipids, rice bran oil polyglyceryl-3 esters, rice oil diglyceryl esters, (Z)—, ricinoleic acid, ricinoleth-40, *Rosa rubiginosa* seed oil peg-8 esters, *Saccharomyces/Stevia rebaudiana* leaf/stem ferment extract, safflower seed oil peg-8 esters, safflower seed oil polyglyceryl-6 esters, *Schinziophyton rautanenii* kernel oil peg-8 esters, *Schinziophyton rautanenii* kernel oil polyglyceryl-6 esters, *Sclerocarya birrea* seed oil peg-8 esters, *Sclerocarya birrea* seed oil polyglyceryl-6 esters, *Sclerocarya birrea* seed oil polyglyceryl-10 esters, sesame oil polyglyceryl-6 esters, sesame seed oil peg-8 esters, sesamide DIPA, shea butter glycereth-8 esters, shea butter glyceride, shea butter peg-8 esters, shea butter peg-32 esters, shea butter polyglyceryl-6 esters, shea butteramidopropyltrimonium chloride, silicone quaternium-17, silicone quaternium-21, sodium avocadoate, sodium beeswax, sodium behenoyl lactylate, sodium bisglycol ricinosulfosuccinate, sodium butoxynol-12 sulfate, sodium butylglucosides hydroxypropyl phosphate, sodium C10-15 pareth sulfate, sodium $C_{11-15}$ pareth-7 carboxylate, sodium $C_{12-13}$ pareth sulfate, sodium $C_{12-13}$ pareth-12 carboxylate, sodium $C_{12-13}$ pareth-5 carboxylate, sodium $C_{12-13}$ pareth-8 carboxylate, sodium $C_{12-14}$ pareth-3 sulfate, sodium $C_{12-15}$ alkyl sulfate, sodium $C_{12-15}$ pareth sulfate, sodium $C_{12-15}$ pareth-15 sulfonate, sodium $C_{12-15}$ pareth-3 sulfonate, sodium $C_{12-15}$ pareth-6 carboxylate, sodium $C_{12-15}$ pareth-7 carboxylate, sodium $C_{12-15}$ pareth-7 sulfonate, sodium $C_{12-15}$ pareth-8 carboxylate, sodium C12-18 alkyl sulfate, sodium C13-15 pareth-8 butyl phosphate, sodium C13-15 pareth-8 phosphate, sodium $C_{14-15}$ pareth-8 carboxylate, sodium C16-20 alkyl sulfate, sodium C9-11 pareth-6 carboxylate, sodium caproyl lactylate, sodium caprylate, sodium capryleth-9 carboxylate, sodium capryloamphohydroxypropylsulfonate, sodium caprylyl sulfonate, sodium carboxydecyl peg-8 dimethicone, sodium carboxymethyl $C_{10-16}$ alkyl glucoside, sodium carboxymethyl chitosan lauramide, sodium castorate, sodium ceteth-13 carboxylate, sodium ceteth-4 phosphate, sodium cetyl sulfate, sodium chitosan cocamide hydroxypropylsulfate, sodium chitosan lauramide hydroxypropylsulfate, sodium coco sulfoacetate, sodium coco-glucoside tartrate, sodium coco/babassu sulfate, sodium coco/hydrogenated tallow sulfate, sodium cocoate, sodium cocoglucosides hydroxypropyl phosphate, sodium cocoglucosides hydroxypropylsulfonate, sodium cocosulfate, sodium cocoyl barley amino acids, sodium cocoyl lactylate, sodium cocoyl threoninate, sodium cocoyl/palmoyl/sunfloweroyl glutamate, sodium cocoyl/stearoyl (alanine/arginine/asparagine/aspartic acid/glutamic acid/glutamine/glycine/histidine/isole, sodium deceth sulfate, sodium deceth-2 carboxylate, sodium decylglucosides hydroxypropylsulfonate, sodium diceteareth-10 phosphate, sodium dilaureth-4 phosphate, sodium dilaureth-7 citrate, sodium dioleth-8 phosphate, sodium glyceryl oleate phosphate, sodium hydroxylauryldimonium ethyl phosphate, sodium hydroxypropylphosphate decylglucoside crosspolymer, sodium hydroxypropylphosphate laurylglucoside crosspolymer, sodium hydroxypropylsulfonate cocoglucoside crosspolymer, sodium hydroxypropylsulfonate decylglucoside crosspolymer, sodium hydroxypropylsulfonate laurylglucoside crosspolymer, sodium isostearate, sodium isosteareth-11 carboxylate, sodium isosteareth-6 carboxylate, sodium isostearoyl lactate, sodium isostearoyl lactylate, sodium lardate, sodium lauraminopropionate, sodium laurate, sodium laureth sulfate, sodium laureth-2 phosphate, sodium laureth-3 carboxylate, sodium laureth-13 carboxylate, sodium laureth-4 phosphate, sodium lauroyl methylaminopropionate, sodium lauryl phosphate, sodium lauryl sulfate, sodium laurylglucosides hydroxypropyl phosphate, sodium laurylglucosides hydroxypropylsulfonate, sodium linoleate, sodium macadamiaseedate, sodium mangoseedate, sodium methoxy ppg-2 acetate, sodium methyl isethionate, sodium methyltaurine cocoyl methyltaurate, sodium myreth sulfate, sodium myristate, sodium myristyl sulfate, sodium octoxynol-2 ethane sulfonate, sodium octoxynol-6 sulfate, sodium octoxynol-9 sulfate, sodium oleoyl lactylate, sodium oleth sulfate, sodium oleth-7 phosphate, sodium oleth-8 phosphate, sodium oleyl sulfate, sodium palmate, sodium peanutate, sodium peg-3 lauramide carboxylate, sodium peg-4 lauramide carboxylate, sodium peg-50 hydrogenated castor oil succinate, sodium peg-6 cocamide carboxylate, sodium peg-8 cocamide carboxylate, sodium propoxy ppg-2 acetate, sodium rapeseedate, sodium ricinoleamidopropyl PG-dimonium chloride phosphate, sodium sesameseedate, sodium soyate, sodium steareth-4 phosphate, sodium stearoamphohydroxypropylsulfonate, sodium stearoyl glutamate, sodium stearoyl lactylate, sodium stearyl dimethyl glycine, sodium stearyl phthalamate, sodium stearyl sulfate, sodium surfactin, sodium sweet almondate, sodium tallate, sodium taurine cocoyl methyltaurate, sodium trideceth sulfate, sodium tridecyl sulfate, sodium undeceth-5 carboxylate, sodium/MEA laureth-2 sulfosuccinate, sodium/MEA-peg-3 cocamide sulfate, sorbeth-2 beeswax, sorbeth-2 cocoate, sorbeth-3 isostearate, sorbeth-3 tristearate, sorbeth-4 tetraoleate, sorbeth-5, sorbeth-6 beeswax, sorbeth-6 hexastearate, sorbeth-6 laurate, sorbeth-6 tetraoleate, sorbeth-7, sorbeth-8 beeswax, sorbeth-20 pentaisostearate, sorbeth-20 tetraisostearate, sorbeth-30 pentaisostearate, sorbeth-30 tetraisostearate, sorbeth-30 tetraoleate laurate, sorbeth-40 pentaisostearate, sorbeth-40 pentaoleate, sorbeth-40 tetraisostearate, sorbeth-50 pentaisostearate, sorbeth-50 tetraisostearate, sorbeth-60 tetrastearate, sorbeth-20 beeswax, sorbeth-30, sorbeth-30 tetraoleate, sorbeth-40, sorbeth-40 tetraoleate, sorbeth-50 hexaoleate, sorbeth-6, sorbeth-60 tetraoleate, isosorbide laurate, sorbitan caprylate, sorbitan cocoate, sorbitan diisostearate, sorbitan dioleate, sorbitan isostearate, sorbitan laurate, sorbitan oleate, sorbitan oleate decylglucoside crosspolymer, sorbitan oleate laurylglucoside crosspolymer, sorbitan olivate, sorbitan palmitate, sorbitan sesquiisostearate, sorbitan sesquioleate (2:3), sorbitan sesquistearate, sorbitan stearate, sorbitan triisostearate, sorbitan trioleate, sorbitan tristearate, sorbitan undecylenate, sorbityl acetate, sorbityl laurate, soy acid, hydrogenated soy polyglycerides/soyamide DEA, soy sterol, soy sterol acetate, soyamide DEA, soyamidopropyl dimethylamine, soyamine, soyaminopropylamine, soybean oil peg-8 esters, soybean oil peg-20 esters, soybean oil peg-36 esters, soybean oil polyglyceryl-6 esters, soytrimonium chloride, stearamidoethyl ethanolamine, isostearamidomorpholine stearate, stearamidopropyl dimethylamine stearate, steardimonium hydroxypropyltrimonium chloride, steareth-1, steareth-2, isosteareth-2, steareth-2 phosphate, steareth-3, isosteareth-3, steareth-4, steareth-5, isosteareth-5, steareth-5 stearate, steareth-6, isosteareth-6 carboxylic acid, steareth-7, steareth-8, steareth-10, isosteareth-10, isosteareth-10 stearate, steareth-11, isosteareth-11 carboxylic acid, steareth-12, isosteareth-12, steareth-13, steareth-14, steareth-15, isosteareth-15, steareth-16, steareth-20, isosteareth-20, steareth-21, isosteareth-22, steareth-25, isosteareth-25, isosteareth-50, isosteareth-2 phosphate, steareth-200, isosteareth-200 palmitate, isostearic/myristic glycerides, stearoamphoacetic acid, stearoyl ethyltrimonium methosulfate, stearoyl inulin, stearoyl lactylic acid, stearoyl leucine, stearyl acetyl glutamate, stearyl alcohol, isostearyl carboxydecyl peg-8 dimethicone, isostearyl glucoside, stearyl olivate, stearyl PG-trimonium chloride, stearyl phosphate, stearyldimoniumhydroxypropyl butylglucosides chloride, stearyldimoniumhydroxypropyl decylglucosides chloride, stearyldimoniumhydroxypropyl laurylglucosides chloride, sucrose cocoate, sucrose dilaurate, sucrose distearate, sucrose hexaerucate, sucrose hexaoleate/hexapalmitate/hexastearate, sucrose hexapalmitate, sucrose mortierellate, sucrose myristate, sucrose oleate, sucrose palmitate, sucrose pentaerucate, sucrose polybehenate, sucrose polycottonseedate, sucrose polylaurate, sucrose polylinoleate, sucrose polypalmate, sucrose polysoyate, sucrose polystearate, sucrose ricinoleate, sucrose tetraisostearate, sucrose tetrastearate triacetate, sucrose tribehenate, sucrose trilaurate, sucrose tristearate, sunflower glycerides citrate, sunflower seed oil glycereth-8 esters, sunflower seed oil glyceride, sunflower seed oil glycerides, sunflower seed oil peg-32 esters, sunflower seed oil peg-8 esters, sunflower seed oil polyglyceryl-10 esters, sunflower seed oil polyglyceryl-3 esters, sunflower seed oil polyglyceryl-4 esters, sunflower seed oil polyglyceryl-5 esters, sunflower seed oil polyglyceryl-6 esters, sunflower seed oil sorbitol esters, hydrogenated tallow acid, tallow amine, acetylated hydrogenated tallow glyceride, hydrogenated tallow glyceride citrate, hydrogenated tallow glyceride lactate, tallow glycerides, acetylated hydrogenated tallow glycerides, hydrogenated tallow glycerides, hydrogenated tallow glycerides citrate, dihydrogenated tallow methylamine, dihydrogenated tallow phthalic acid amide, tallowaminopropylamine, tallowdimonium propyltrimonium dichloride, talloweth-5, talloweth-7, hydrogenated talloweth-12, talloweth-18, hydrogenated talloweth-25, hydrogenated talloweth-60 myristyl glycol, talloweth-4, talloweth-6, TEA-$C_{11-15}$ pareth sulfate, TEA-$C_{12-13}$ pareth-3 sulfate, TEA-canolate, TEA-cocoate, TEA-cocoyl glycinate, TEA-dextrin octenylsuccinate, TEA-diethanolaminoethyl polyisobutenylsuccinate, TEA-dimethicone peg-7 phosphate, TEA-isostearate, TEA-laneth-5 sulfate, TEA-laurate, TEA-laurate/myristate, TEA-laureth sulfate, TEA-laureth-4 phosphate, TEA-lauroyl lactylate, TEA-lauryl sulfate, TEA-myristate, TEA-oleate, TEA-oleyl sulfate, TEA-palmitate, TEA-peg-3 cocamide sulfate, TEA-peg-50 hydrogenated castor oil succinate, TEA-stearate, TEA-tallate, tetrasodium dicarboxyethyl stearyl sulfosuccinamate, *Theobroma grandiflorum* seed butter glyceryl esters, *Theobroma grandiflorum* seed butter peg-8 esters, *Theobroma grandiflorum* seed butter polyglyceryl-6 esters, TIPA-lauryl sulfate, TIPA-stearate, tocopheryl phosphate, tri-$C_{12-15}$ pareth-10 phosphate, tri-$C_{12-15}$ pareth-2 phosphate, tri-$C_{12-15}$ pareth-6 phosphate, tri-$C_{12-15}$ pareth-8 phosphate, triarachidin, tribehenin peg-20 esters, triceteareth-4 phosphate, triceteth-5 phosphate, *Trichilia emetica* seed oil peg-8 esters, *Trichilia emetica* seed oil polyglyceryl-6 esters, trideceth-2, trideceth-3, trideceth-3 phosphate, trideceth-4, trideceth-5, trideceth-6, trideceth-6 phosphate, trideceth-7, trideceth-8, trideceth-9, trideceth-10 phosphate, trideceth-12, trideceth-15, trideceth-15 carboxylic acid, trideceth-18, trideceth-20, trideceth-50, trifluoropropyl dimethicone/peg-10 crosspolymer, trilaneth-4 phosphate, trilaureth-4 phosphate, trilaureth-9 citrate, triolein peg-6 esters, trioleth-8 phosphate, undecanoic acid dimethicones, undeceth-3, undeceth-5, undeceth-7, undeceth-8, undeceth-9, undeceth-11, hydrolyzed VA/vinyl acetoacetate copolymer, hydrogenated vegetable glycerides, hydrogenated vegetable glycerides citrate, vegetable glycerides phosphate, hydrogenated vegetable glycerides phosphate, watermelon seed oil peg-8 esters, watermelon seed oil polyglyceryl-10 esters, watermelon seed oil polyglyceryl-6 esters, wheat germ oil glycereth-8 esters, wheat germ oil peg-8 esters, xanthan gum, ximenia americana seed oil peg-8 esters, ximenia americana seed oil polyglyceryl-6 esters, zinc coceth sulfate, zinc coco-sulfate, and mixtures thereof.

The lotion may also comprise a thickener. A thickener helps to keep the lotion stable. A thickener also helps in making the lotion more appealing to use. Examples of thickeners include agar, algin (*Laminaria* spp. and other kelps), alginic acid, alumina magnesium metasilicate, ammonium alginate, *Astragalus* gummifer gum, attapulgite, biotite, *Aaesalpinia spinosa* gum, calcium alginate, calcium carrageenan, carrageenan, cassia gum, cellulose, cellulose regenerated, *Cyamopsis tetragonoloba* gum, dextrin, ethyl hydroxyethyl cellulose, gellan gum, ghatti gum, hydrogenated rapeseed oil, lithium magnesium silicate, lithium magnesium sodium silicate, methyl ethyl cellulose, pectin, potassium alginate, potassium carrageenan, propylene glycol alginate, sodium carboxymethyl cellulose, sodium carrageenan, sodium hydroxypropyl starch phosphate, sodium magnesium silicate, sodium sulfate, *Sterculia urens* gum, synthetic fluorphlogopite, vinyl dimethyl/trimethylsiloxysilicate stearyl dimethicone crosspolymer, vinyldimethyl/trimethylsiloxysilicate stearyl dimethicone crosspolymer, xanthan gum, and mixtures thereof.

The lotion may also comprise a fragrance. A fragrance may be used to provide a smell to the lotion prior to the application by the patient to the patient's skin for aesthetic purposes. Alternatively, or additionally, a fragrance may be used to provide a lingering smell after the application of the lotion onto the skin of the patient. Examples of frangrances that may be used include abronia fragrance, acacia fragrance, agate fragrance, aldehydic fragrance, allspice fragrance, almond fragrance, aloe fragrance, aloe vera fragrance, amaretto coffee fragrance, amber floral fragrance, amber fragrance, sports amber fragrance, amber nutmeg fragrance, amber powdery floral fragrance, amber romance fragrance, ambergris fragrance, ambreine fragrance, ambrosia fragrance, angel dust fragrance, angel essence fragrance, angel feathers fragrance, angel wings fragrance, animal fragrance, anise fragrance, apple blossom fragrance, apple butter fragrance, apple cider fragrance, apple cinnamon fragrance, apple cranberry fragrance, apple crisp fragrance, apple fragrance, baked apple fragrance, candy apple fragrance, green apple fragrance, red apple fragrance, apple pear fragrance, apple pie fragrance, apple spice fragrance, apricot almond fragrance, apricot fragrance, apricot mango fragrance, apricot peach fragrance, aromatic fragrance, aromatic woody citrus floral fragrance, autumn fragrance, avocado fragrance, azalea fragrance, baby powder fragrance, bacon fragrance, balsam fragrance, bamboo fragrance, banana cream pie fragrance, banana fragrance, banana nut bread fragrance, banana nut cake fragrance, banana pudding fragrance, bay rum fragrance, bayberry fragrance, bergamot blossom fragrance, bergamot fragrance, berry fragrance, china berry fragrance, wild berry fragrance, berry jam fragrance, bird of paradise fragrance, blackberry fragrance, blackberry vanilla fragrance, blue grass fragrance, blue lagoon fragrance, blueberry fragrance, blueberry muffin fragrance, blueberry pie fragrance, bois de rose fragrance, boronia fragrance, bouquet fragrance, bouvardia fragrance, boysenberry fragrance, brazil nut fragrance, baked bread fragrance, briar wood fragrance, bubble gum fragrance, butter cream fragrance, butter fragrance, butter rum fragrance, butter vanilla fragrance, butterscotch fragrance, cactus blossom fragrance, cake fragrance, pound cake fragrance, red velvet cake fragrance, spice cake fragrance, camellia fragrance, cananga fragrance, candle fragrance, candy cane fragrance, candy corn fragrance, cantaloupe fragrance, cappuccino fragrance, caramel corn fragrance, caramel fragrance, carnation fragrance, carrot cake fragrance, cashmere fragrance, cassia fragrance, castoreum fragrance, cedar forest fragrance, cedar fragrance, cedarwood fragrance, chamomile fragrance, champaca fragrance, cherry berry fragrance, cherry blossom fragrance, cherry blossom soap fragrance, cherry fragrance, black cherry fragrance, sour cherry fragrance, wild cherry fragrance, roasted chestnut fragrance, chocolate cherry fragrance, chocolate chip cookie fragrance, chocolate fragrance, dark chocolate fragrance, white chocolate fragrance, chocolate hazelnut fragrance, chocolate mint fragrance, chocolate orange fragrance, chocolate raspberry fragrance, christmas fragrance, chrysanthemum fragrance, chypre fragrance, cinnamon bun fragrance, cinnamon cookie fragrance, cinnamon fragrance, cinnamon spice fragrance, citronella fragrance, citrus basil fragrance, citrus bergamot fragrance, citrus floral fragrance, citrus floral green fragrance, citrus fragrance, citrus ginger fragrance, citrus green fragrance, citrus herbal fragrance, citrus linen fragrance, citrus mint fragrance, citrus rose fragrance, citrus sage fragrance, citrus vanilla fragrance, citrus woody floral fragrance, citrus woody fragrance, civet fragrance, clean linen fragrance, clematis fragrance, clove fragrance, clover fragrance, cocoa butter fragrance, cocoa fragrance, coconut cream pie fragrance, coconut fragrance, tropical coconut fragrance, coconut kiwi fragrance, coconut lime fragrance, coconut lime verbena fragrance, coconut mango fragrance, coconut papaya fragrance, coffee fragrance, cognac fragrance, cologne fragrance, colonia fragrance, cookie dough fragrance, cornucopia fragrance, coronilla fragrance, cotton candy fragrance, clean cotton fragrance, sea cotton fragrance, country meadow fragrance, crabapple blossom fragrance, cranberry fragrance, cranberry orange spice fragrance, cranberry spice fragrance, cream fragrance, crème brulee fragrance, cucumber fragrance, cucumber melon fragrance, cucumber rose melon fragrance, currant fragrance, black currant fragrance, red currant fragrance, cyclamen fragrance, daffodil fragrance, daisy fragrance, daphne fragrance, date fragrance, deodorant fragrance, dianthus fragrance, dillenia fragrance, dogwood fragrance, dragons blood fragrance, earth fragrance, egg nog fragrance, eglantine fragrance, elder berry fragrance, elder flower fragrance, evergreen fragrance, fagonia fragrance, fennel fragrance, fern fragrance, fetes fragrance, fig fragrance, filbert fragrance, fine fragrance, fir balsam fragrance, fir tree fragrance, floral aldehydic fragrance, floral bouquet fragrance, floral fragrance, citrus floral fragrance, fruity floral fragrance, green floral fragrance, spicy floral fragrance, woody floral fragrance, floral fruity fragrance, floral green fragrance, floral musk fragrance, floral oriental fragrance, floral powdery fragrance, floral spice fragrance, floral woody fragrance, flower shop fragrance, forest fragrance, forget me not fragrance, fougere herbal fragrance, fougere woody fragrance, frankincense fragrance, freesia fragrance, fresh & clean fragrance, fruit cocktail fragrance, fruit fragrance, fruity green fragrance, fungus fragrance, gardenia fragrance, gardenia lily fragrance, genet fragrance, geranium fragrance, ginger fragrance, white ginger fragrance, ginger lily fragrance, ginger peach fragrance, ginger spice oatmeal fragrance, ginger vanilla fragrance, gingerbread fragrance, gooseberry fragrance, gourmand fragrance, graham cracker fragrance, grape fragrance, concord grape fragrance, grapefruit fragrance, grapefruit ginger fragrance, grapefruit mango fragrance, grapefruit sage fragrance, green grass fragrance, sweet grass fragrance, green fragrance, spring green fragrance, green herbal fragrance, green leaf fragrance, greenhouse fragrance, grenadine fragrance, guava fragrance, guava tangerine fragrance, habuba fragrance, hair care fragrance, hawthorn fragrance, hazelnut coffee fragrance, hazelnut cream fragrance, hazelnut fragrance, heather fragrance, heliotrope fragrance, herbal fragrance, hibiscus fragrance, hollyberry fragrance, home care fragrance, honey almond fragrance, honey fragrance, honey rose fragrance, honeydew fragrance, honeysuckle fragrance, hop fragrance, huckleberry fragrance, hyacinth fragrance, hydrangea fragrance, incense fragrance, iris blossom fragrance, ivy fragrance, jasmin carnation fragrance, jasmin fragrance, jasmin muguet fragrance, jasmin vanilla fragrance, jonquil fragrance, juicy fragrance, juicy fruit fragrance, juniper berry fragrance, juniper fragrance, juniper sage fragrance, kewda fragrance, keylime pie fragrance, kiwi coconut fragrance, kiwi fragrance, kiwi strawberry fragrance, kumquat fragrance, lavandin fragrance, lavender blossom fragrance, lavender fougere fragrance, lavender fragrance, lavender vanilla fragrance, leather fragrance, russian leather fragrance, leather woody fragrance, lemon balm fragrance, lemon bergamot fragrance, lemon blossom fragrance, lemon chiffon fragrance, lemon cucumber fragrance, lemon fragrance, lemon lime fragrance, lemon pie fragrance, lemon thyme fragrance, raspberry lemonade fragrance, lemongrass fragrance, licorice fragrance, lilac fragrance, lily fragrance, calla lily fragrance, water lily fragrance, lily of the valley fragrance, key lime cream fragrance, lime fragrance, lime sherbet fragrance, linden blossom fragrance, loganberry fragrance, lotus fragrance, lychee fragrance, mace fragrance, magnolia fragrance, maja fragrance, malt fragrance, mandarin fragrance, clementine mandarin fragrance, mandarin lemon fragrance, mandarin rose fragrance, mango citrus fragrance, mango flower fragrance, mango fragrance, mango mandarin fragrance, mango melon fragrance, mango peach fragrance, maple fragrance, lime margarita fragrance, marine fragrance, marzipan fragrance, meadowsweet fragrance, medicated fragrance, melon fragrance, citrus melon fragrance, midnight passion fragrance, milk fragrance, mimosa fragrance, mint fragrance, mistletoe fragrance, mocha fragrance, mock orange fragrance, morning glory fragrance, moss fragrance, moss rose fragrance, mulberry fragrance, mulberry spice fragrance, muscadine fragrance, musk fragrance, china musk fragrance, citrus musk fragrance, dark musk fragrance, egyptian musk fragrance, floral musk fragrance, fruity musk fragrance, jasmin musk fragrance, light musk fragrance, oriental musk fragrance, woody musk fragrance, myrrh fragrance, narcissus fragrance, nectar fragrance, neroli fragrance, new mown hay fragrance, nutmeg fragrance, oatmeal milk & honey fragrance, oatmeal raisin cookie fragrance, orange blossom fragrance, orange chiffon fragrance, orange cinnamon fragrance, orange clove fragrance, orange cranberry fragrance, orange cream fragrance, orange fragrance, orange ginger fragrance, orange marmalade fragrance, orange sherbet fragrance, orange spice fragrance, orange vanilla fragrance, orchid fragrance, orchid magnolia fragrance, oriental aldehydic fragrance, oriental citrus fragrance, oriental fragrance, oriental powdery fragrance, orris fragrance, osmanthus fragrance, fresh outdoors fragrance, pansy fragrance, papaya fragrance, papaya mango fragrance, papaya saffron fragrance, parijat fragrance, passion blossom fragrance, passion fruit fragrance, patchouli fragrance, patchouli woody amber fragrance, peach blossom fragrance, peach fragrance, peach pecan fragrance, peaches and cream fragrance, peanut butter cookie fragrance, peanut fragrance, pear berry fragrance, pear blossom fragrance, pear fragrance, pear spice fragrance, pecan pie fragrance, peony fragrance, peppermint fragrance, personal wash fragrance, petitgrain fragrance, petunia fragrance, phlox fragrance, pina colada fragrance, pine bouquet fragrance, pine forest fragrance, pine fragrance, christmas pine fragrance, pineapple fragrance, pinion fragrance, pistachio fragrance, pizza fragrance, plum fragrance, mirabelle plum fragrance, plumeria fragrance, pointsettia fragrance, pomegranate fragrance, popcorn fragrance, red poppy fragrance, potpourri fragrance, powder fragrance, powdery animal fragrance, pralines and cream fragrance, primrose fragrance, prune fragrance, pumpkin fragrance, pumpkin pie fragrance, pumpkin spice fragrance, quince fragrance, quince rum fragrance, rain forest fragrance, rain fragrance, china rain fragrance, spring rain fragrance, raisin fragrance, raspberry fragrance, black raspberry fragrance, reseda fragrance, rhubarb fragrance, rice flower & shea fragrance, root beer fragrance, rose d'orient fragrance, rose fragrance, desert rose fragrance, dog rose fragrance, red rose fragrance, tea rose fragrance, white rose fragrance, rose geranium fragrance, rose jasmin fragrance, rose musk fragrance, rose otto fragrance, rose petal fragrance, rose raspberry fragrance, rose woody fragrance, rosemary fragrance, rosemary mint fragrance, rum fragrance, saffron fragrance, sage fragrance, desert sage fragrance, sandalwood fragrance, vanilla sandalwood fragrance, sassafras fragrance, scented stock fragrance, sea breeze fragrance, shalimar fragrance, sherry fragrance, skin care fragrance, smoke fragrance, soapy sandalwood moss fragrance, spearmint fragrance, spice fragrance, christmas spice fragrance, country spice fragrance, vanilla spice fragrance, spicy kitchen fragrance, spring flowers fragrance, spruce fragrance, stephanotis fragrance, strawberries and cream fragrance, strawberry fragrance, strawberry peach fragrance, sugar cookie fragrance, sugar fragrance, brown sugar fragrance, sunflower fragrance, sweet pea fragrance, tangerine fragrance, tangerine ginger fragrance, white tea and ginger fragrance, tea fragrance, black tea fragrance, chai tea fragrance, green tea fragrance, lemon tea fragrance, orange pekoe tea fragrance, white tea fragrance, teak fragrance, tobacco flower fragrance, tobacco fragrance, toffee fragrance, toilet waters, tomato leaf fragrance, tuberose fragrance, tulip fragrance, tutti frutti fragrance, vanilla fragrance, vanilla bean fragrance, vanilla cream fragrance, vanilla fragrance, country vanilla fragrance, french vanilla fragrance, vanilla hazelnut fragrance, verbena fragrance, vetiver fragrance, violet fragrance, violet leaf fragrance, violet shea fragrance, wallflower fragrance, walnut fragrance, watermelon fragrance, bourbon whiskey fragrance, wine fragrance, wintergreen fragrance, wisteria fragrance, witch hazel fragrance, woody aldehydic fragrance, woody amber fragrance, woody bouquet fragrance, woody fragrance, woody fruity fragrance, woody herbal fragrance, woody musk fragrance, woody oriental fragrance, woody powdery fragrance, yew fragrance, ylang ylang fragrance, yuzu fragrance, yuzu mint fragrance, and mixtures thereof.

The lotion may also comprise a colorant. A colorant may be used to provide a tinge the lotion prior to the application by the patient to the patient's skin for aesthetic purposes. Alternatively, a colorant may be used to provide color the lotion prior to the application by the patient to the patient's skin for identification purposes. Alternatively, or additionally, a colorant may be used to provide a coloring effect on the skin of the patient after the application of the lotion onto the skin of the patient.

The topical composition of the present invention is prepared by mixing sequentially into a skin lotion (a) solid vinylpyrrolidone/vinyl acetate copolymer, and (b) vinylpyrrolidone/vinyl acetate copolymer dissolved in a solvent.

The steps for preparing the topical composition of the present invention include: preparing base skin lotion, adding to it solid vinylpyrrolidone/vinyl acetate copolymer, and then adding to that vinylpyrrolidone/vinyl acetate copolymer dissolved in a solvent.

Alternatively, the steps for preparing the topical composition of the present invention include: preparing base skin lotion, adding to it vinylpyrrolidone/vinyl acetate copolymer dissolved in a solvent, and then adding to that solid vinylpyrrolidone/vinyl acetate copolymer.

The term "sequentially" means that ingredients (a) and (b) are not added at the same time, but one after each other, in any suitable order. Under one embodiment ingredient (a) is added first, and then ingredient (b) is added. Under another embodiment ingredient (b) is added first, and then ingredient (a) is added.

The present invention is also related to a topical composition for use in reducing exposure of gaseous pollutants to skin, prepared by mixing sequentially into a skin lotion (a) solid vinylpyrrolidone/vinyl acetate copolymer, and (b) vinylpyrrolidone/vinyl acetate copolymer dissolved in a solvent, wherein the composition is a fully formulated topical lotion for use in reducing exposure of gaseous pollutants to skin of a patient.

The term "fully formulated" means that the lotion is ready for use by the patient.

Under one embodiment the topical composition of the present invention is used like any common cream, gel, or body lotion. The topical composition may be spread on a patient's skin like any other typical cream, gel, or body lotion. It may be spread with the patient's hand or any suitable device. The topical composition is spread at about a 20-micrometer layer. Under another embodiment, the topical composition is spread in a layer of 30 micrometers or more. Under another embodiment, the topical composition is spread in a layer of 15 micrometers or less. Under an embodiment, the topical composition is spread in a layer of 10 to 50 micrometers.

It has been observed that the addition of solid vinylpyrrolidone/vinyl acetate copolymer, wherein the vinylpyrrolidone:vinyl acetate ratio of 60:40, and mean molecular weight of 51,000 (PVP/VA S-630, supplied by Ashland, hereinafter "S-630") at 1.0 wt % in a lotion exhibits ozone blocking at about 11%. It has been observed that the addition of vinylpyrrolidone/vinyl acetate copolymer dissolved in pure ethanol in a 50 wt % ratio, wherein the vinylpyrrolidone:vinyl acetate ratio of 70:30, and mean molecular weight of 56,700 (PVP/VA E-735, supplied by Ashland, hereinafter "E-735") at 1.0 wt % in a lotion exhibits ozone blocking at about 10%. However, it has been observed that the addition of both solid vinylpyrrolidone/vinyl acetate copolymer S-630, and dissolved vinylpyrrolidone/vinyl acetate copolymer E-735, each at 1 wt % level in a lotion, exhibits ozone blocking at about 32%. This is an unusual and unexpected large increase in the ozone blocking ability of the lotion that comprises the solid and dissolved vinylpyrrolidone/vinyl acetate copolymer. This large increase is repeatable, and is statistically significant.

Under one embodiment, the composition of the present invention reduces the transmission of ozone by at least 20% compared to the composition without the solid vinylpyrrolidone/vinyl acetate copolymer and the vinylpyrrolidone/vinyl acetate copolymer dissolved in a solvent. Under one embodiment, the composition of the present invention reduces the transmission of ozone by at least 20% compared to the composition without the solid vinylpyrrolidone/vinyl acetate copolymer. Under one embodiment, the composition of the present invention reduces the transmission of ozone by at least 20% compared to the composition without the vinylpyrrolidone/vinyl acetate copolymer dissolved in a solvent.

The observed synergistic effect in the ozone blocking is repeatable and statistically significant. Unfortunately, the theoretical underpinnings of the observed behavior is elusive. While the lotion comprising both S-630 and E-735 exhibit a slight bimodal molecular weight distribution, and exhibit a slight differences in the PV:VA ratios, it is more likely that the explanation lies in the state at which the copolymer is added to the lotion.

The present invention is also directed to a method for reducing exposure of gaseous pollutants to skin of a patient for skin, comprising applying to an area of skin the topical composition prepared by mixing sequentially into a skin lotion (a) solid vinylpyrrolidone/vinyl acetate copolymer, and (b) vinylpyrrolidone/vinyl acetate copolymer dissolved in a solvent. Under one embodiment of this method, the weight ratio of the copolymer content of (a) to (b) is about 8:1 to about 0.4:1. Under one embodiment of this method, the weight ratio of the copolymer content of (a) to (b) is about 6:1 to about 0.67:1. Under one embodiment of this method, the weight ratio of the copolymer content of (a) to (b) is about 3:1 to about 1:1. Under one embodiment of this method, the solid vinylpyrrolidone/vinyl acetate copolymer has a molecular weight in the range of about 10,000 g/mol to about 100,000 g/mol. Under one embodiment of this method, the solid vinylpyrrolidone/vinyl acetate copolymer has a molecular weight in the range of about 30,000 g/mol to about 70,000 g/mol. Under one embodiment of this method, the vinylpyrrolidone/vinyl acetate copolymer dissolved in the solvent has a molecular weight in the range of about 10,000 g/mol to about 100,000 g/mol. Under one embodiment of this method, the vinylpyrrolidone/vinyl acetate copolymer dissolved in the solvent has a molecular weight in the range of about 30,000 g/mol to about 70,000 g/mol. Under one embodiment of this method, the solvent is selected from the group consisting of alcohols, esters, and ketones. Under one embodiment of this method, the solvent is selected from the group consisting of ethanol, n-propanol, i-propanol, methyl acetate, ethyl acetate, methyl propionate, ethyl propionate, acetone, methyl ethyl ketone, and 3-pentone. Under one embodiment of this method, the solvent is ethanol. Under one embodiment of this method, the composition further comprises water, a humectant, a preservative, an exfoliator, a lubricant, an emollient, and an emulsifier. Under one embodiment of this method, the composition is a fully formulated topical lotion for use in reducing exposure of gaseous pollutants to skin of a patient. Under one embodiment of this method, a 20-micrometer layer of the composition reduces the transmission of ozone by at least 20% compared to the composition without the solid vinylpyrrolidone/vinyl acetate copolymer and the vinylpyrrolidone/vinyl acetate copolymer dissolved in a solvent. Under one embodiment of this method, a 20-micrometer layer of the composition reduces the transmission of ozone by at least 20% compared to the composition without the solid vinylpyrrolidone/vinyl acetate copolymer. Under one embodiment of this method, a 20-micrometer layer of the composition reduces the transmission of ozone by at least 20% compared to the composition without the vinylpyrrolidone/vinyl acetate copolymer dissolved in a solvent.

The method comprises the steps of placing the topical composition onto a small portion of a patient's skin, and spreading the topical composition onto a larger section of the patient's skin to form a layer of the topical composition. Alternatively, the method comprises the steps of placing the topical composition onto a patient's hand, and spreading the topical composition onto a larger section of the patient's skin to form a layer of the topical composition. Alternatively, the method comprises the steps of placing the topical composition onto a device, and spreading the topical composition onto a larger section of the patient's skin to form a layer of the topical composition.

The topical composition may be spread on a patient's skin with the patient's hand or any suitable device. The topical composition is spread at about a 20-micrometer layer. Under another embodiment, the topical composition is spread in a layer of 30 micrometers or more. Under another embodiment, the topical composition is spread in a layer of 15 micrometers or less. Under an embodiment, the topical composition is spread in a layer of 10 to 50 micrometers.

The present invention is also directed to a method of evaluating the reduction of the transmission of harmful pollutants to a patient's skin.

Specifically, the method used to evaluate the reduction of the transmission of harmful pollutants to a patient's skin by the use of investigational ingredients in a representative topical composition ("lotion") is modeled on the transmission of ozone through the lotion which comprises the investigational ingredients to an animal model skin.

The ozone decay model is used to determine the ozone blocking performance of the lotion. The goal of this method is to extract the kinetic rate constant of ozone decomposition in the presence of a reactive substrate. The reactive substrate used in this method is an animal skin that approximates that of a human. Under one embodiment, the method uses a 5 cm×5 cm porcine skin coupon.

The ozone decomposition inside of a ozone chamber is modeled by the following mole balance:

$$\frac{d[O_3]}{dt} = r_{in} - r_{out} + r_{gen} - r_{conspn} \quad (1)$$

wherein $r_{in}$ is the rate of infusion, $r_{out}$ is the rate of effusion, $r_{gen}$ is the rate of generation, and $r_{conspn}$ is the rate of consumption of ozone.

Because this method focuses only on the decay curve of ozone, the ozone generator is turned off once the ozone concentration inside the chamber reaches 800 ppb. Hence, the first 3 terms in the can be neglected. Equation (1) then becomes:

$$\frac{d[O_3]}{dt} = r_{in} - r_{out} + r_{gen} - r_{decomp} - r_{rxn} \quad (2)$$

The consumption of ozone is accounted for by the rate of decomposition $r_{decomp}$ and the rate of reaction $r_{rxn}$. The rate of decomposition $r_{decomp}$ is the background decomposition of ozone that is characteristic of the chamber in the absence of a reactive substrate through carulite granular catalysts. The rate of reaction $r_{rxn}$ is the consumption of ozone by the reaction with the reactive substrate. Equation (2) can be further broken down in terms of concentration.

$$\frac{d[O_3]}{dt} = -k_d[O_3]^\alpha - k_{rxn}[s]^\beta \cdot [O_3]^\gamma \quad (3)$$

wherein $[O_3]$ is the concentration of ozone, $[s]$ is the concentration of the reactive species in the pig skin, $k_d$ is the rate constant of the background decomposition of ozone that is characteristic of the chamber, $k_{rxn}$ is the rate constant of the consumption of ozone by the reaction with the reactive substrate, and $\alpha$, $\beta$, and $\gamma$ are their respective reaction orders.

To determine the reaction order $\alpha$, the background decomposition of ozone in the chamber in absence of the reactive substrate is measured and regression of equation (5) is performed.

$$\frac{d[O_3]}{dt} = -k_d[O_3]^\alpha \quad (4)$$

Under some embodiments, a regression of $\ln(d[O_3]/dt)$ vs. $\ln[O_3]$ in the absence of a reactive substrate is linear, indicating a first order reaction rate, thus $\alpha=1$.

$$\ln\left[-\frac{d[O_3]}{dt}\right] = \ln k_d + \alpha \cdot \ln[O_3] \quad (5)$$

To determine the reaction order $\gamma$, the $O_3$ concentration profile in the presence of the reactive substrate is measured. A similar regression analysis from above is performed as shown in equation (6).

$$\frac{d[O_3]}{dt} = -k_d[O_3]^\alpha - k_{rxn}[s]^\beta \cdot [O_3]^\gamma \quad (6)$$

Under some embodiments, the regression $\ln(-d[O_3]/dt)$ vs. $\ln[O_3]$ in the presence of a reactive substrate yields a straight line, indicating that the overall order of the decomposition is equal to 1 with respect to the concentration of O3. Under such embodiments, it may be concluded that γ=1 and the rate of the decomposition of ozone does not depend on the concentration of the reactive species in the substrate. This may be interpreted that the effective concentration of the reactive species [s] on the pig skin is much greater than the concentration of ozone. Under such embodiments, the ozone concentration is rate controlling and not the concentration of reactive species [s]. The equation (3) may be simplified to:

$$\frac{d[O_3]}{dt} = -(k_d + (k_{rxn}[s]^\beta)) \cdot [O_3]^\gamma \quad (7)$$

$$\frac{d[O_3]}{dt} = -(k_d + (k'_{rxn})) \cdot [O_3]^1 \quad (8)$$

$$\frac{d[O_3]}{dt} = -k_{app}[O_3] \quad (9)$$

Integrating both sides of the equations results in:

$$\int_0^{[O_3]} \frac{d[O_3]}{[O_3]} = -\int_o^t k_{app} dt \quad (10)$$

$$\ln\frac{[O_3]^0}{[O_3]} = k_{app} t \quad (11)$$

Under some embodiments, the model reduces to Equation (11). Concentration profile from the experiment can be directly regressed into this equation to determine $k_{app}$. The reaction rate constant $k_{app}$ is the combination of the rate constant of the background decomposition of ozone that is characteristic of the chamber $k_d$ and the rate constant of the consumption of ozone by the reaction with the reactive substrate $k_{rxn}'$ assuming that [s] is not rate limiting.

This above-described model may be used to evaluate the efficacy of blocking the transmission of harmful pollutants. Under one embodiment, the procedure for the evaluation of the blocking effects of various ingredients in lotions may be undertaken in a series of steps including the following: (a) prepare the lotion; (b) load the lotion onto a coupon model of human skin; (c) expose the loaded coupon to an ozone-enriched atmosphere; (d) calculate the ozone transmission through the lotion.

EXAMPLES

The above model was used to evaluate the blocking efficiency of ozone in a base topical composition. The base topical composition was a commercially available body lotion.

Example 1

Three experimental batches of lotions were prepared. In the first batch, 1.0 wt % of solid vinylpyrrolidone/vinyl acetate copolymer, wherein the vinylpyrrolidone:vinyl acetate ratio of 60:40, and mean molecular weight of 51,000 (PVP/VA S-630, supplied by Ashland, hereinafter "S-630") was mixed into the base topical composition. In the second batch, 1.0 wt % of vinylpyrrolidone/vinyl acetate copolymer dissolved in pure ethanol in a 50 wt % ratio, wherein the vinylpyrrolidone:vinyl acetate ratio of 70:30, and mean molecular weight of 56,700 (PVP/VA E-735, supplied by Ashland, hereinafter "E-735") was mixed into the base topical composition. In the third batch, 1.0 wt % of S-630 and 1.0 wt % of E-735 were mixed sequentially into the base topical composition.

For each run about 50 mg of a formulated lotion was loaded in the middle of a 5×5 cm porcine skin coupon (Animals Technology, Inc., Bozman, Maryland, USA), and was spread on the entire surface of the coupon using an index finger. This procedure resulted in the entire surface of the coupon being coated with about 20 μm layer of lotion.

The loaded coupon was then incubated for 30 minutes at 37° C. to allow water evaporation from the lotion. Such incubation modeled the typical conditions of lotion as used by patients.

The loaded coupon was placed into an ozone chamber (Oxidation Technologies, LLC., Inwood, Indian, USA), and the ozone level of the atmosphere in the chamber was increased to over 800 ppb. The 800 ppb ozone level is the typical high levels of tropospheric ozone observed in highly polluted cities on hot summer days.

Once the concentration of ozone is over 800 ppb, the introduction or generation of ozone in the chamber is stopped, and the level was left to decay. Once the concentration of ozone decreases to 800 ppb, a stopwatch was started. The concentration was then recorded every 30 seconds for 10 minutes or longer.

The above procedure was repeated three or four times with each of the three lotions. The above model was then used to calculate the % of ozone that was blocked by the use of the lotion. The results are presented in the following table.

TABLE 1

| Run | E-735 1 wt % | S-630 1 wt % | S-630 & E-735 1 wt %:1 wt % |
|---|---|---|---|
| 1 | 12.4 | 16.71 | 33.3 |
| 2 | 6.6 | 6.6 | 23.2 |
| 3 | 11.6 | 9.07 | 32.0 |
| 4 | — | — | 37.4 |
| Mean | 10.2 | 10.8 | 31.5 |
| Stand Dev | 3.2 | 5.3 | 6.0 |

The data described in Table 1 (above) demonstrates that the use of E-735 and S-630 individually in the base lotion, had a small, yet statistically significant, impact on the ozone blocking effect. The data in Table 1 (above) also shows that the use of E-735 and S-630 in combination, in the base lotion, had a surprisingly significant impact on the lotion's ozone blocking effect.

Example 2

Three additional experimental batches of lotions were prepared. In the fourth batch, 0.75 wt % of S-630 and 0.75 wt % of E-735 were mixed sequentially into the base topical composition. In the fifth batch, 1.5 wt % of S-630 and 0.5 wt % of E-735 were mixed sequentially into the base topical composition. In the sixth batch, 0.5 wt % of S-630 and 1.5 wt % of E-735 were mixed sequentially into the base topical composition.

These batches were then applied to porcine coupons, incubated, and treated in an ozone chamber in a similar manner as described above.

The above model was then used to calculate the % of the ozone that was blocked by the use of the lotion. The results for the third through sixth batches are presented in the following table.

TABLE 2

| Run | 0.75 wt % S-630 0.75 wt % E-735 | 1.00 wt % S-630 1.00 wt % E-735 | 0.50 wt % S-630 1.50 wt % E-735 | 1.50 wt % S-630 0.50 wt % E-735 |
|---|---|---|---|---|
| 1 | 24.0 | 33.3 | 52.8 | 46.5 |
| 2 | 23.9 | 23.2 | 45.1 | 42.8 |
| 3 | — | 32.0 | — | — |
| 4 | — | 37.4 | — | — |
| Mean | 23.9 | 31.5 | 48.9 | 45.7 |
| Stand Dev | 0.1 | 6.0 | 5.5 | 2.6 |

The data described in Table 2 demonstrates the unexpected impact on ozone blocking effect provided by varying the ratio of the solid PVP/VA copolymer and the dissolved PVP/VA copolymer.

Example 3

Additional experiments with various combinations of polymers were conducted in accordance with the methods described above in Examples 1 and 2. These experiments involved a PVP/VA copolymer alone, and the following polymer combinations:
  Combination 1: 1% PVP/VA copolymer (Plasdone™ S-630)+1% VP/Eicosene Copolymer (Unimer U-15)
  Combination 2: 1% PVP/VA copolymer (Plasdone™ S-630)+1% VP/Hexadecene Copolymer and Octyldodecanol mixture (Unimer U-1946)
  Combination 3: 1% PVP/VA copolymer (Plasdone™ S-630)+1% Acrylic Acid polymer (Noverite™ K-752)
  Combination 4: 1% PVP/VA copolymer (Plasdone™ S-630)+1% Myristamidopropyl PG-Dimonium Chloride Phosphate (Arlasilk™ PTM)
  Combination 5: 1% PVP/VA copolymer (Plasdone™ S-630)+1% Acrylates Copolymer Dermacryl® AQF The results of these experiments are described in Table 3 (below).

TABLE 3

| Sample | Ozone Blocking (%) |
|---|---|
| 1% PVP/VA copolymer | 10.8 |
| 1% VP/Eicosene Copolymer | 15 |
| 1% VP/Hexadecene Copolymer and Octyldodecanol Mixture | −3 |
| 1% Acrylic Acid Polymer | −3 |
| 1% Myristamidopropyl PG-Dimonium Chloride Phosphate | 6 |
| 1% Acrylates Copolymer | 15 |
| Combination 1 | 17 |
| Combination 2 | 5 |
| Combination 3 | 12 |
| Combination 4 | 19 |
| Combination 5 | 15 |

The data described in Table 3 (above) underscores the surprising results delivered by the inventive polymer combinations of the present invention.

While the present invention has been described with reference to several embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention is to be determined from the claims appended hereto. Further, it will be apparent to those of skill in the art that numerous changes may be made in such details without departing from the spirit and the principles of the invention.

The invention claimed is:

1. A personal care composition for use in reducing exposure of gaseous pollutants to skin comprising:
   (a) a first vinylpyrrolidone/vinyl acetate copolymer having a molecular weight in the range of from about 30,000 g/mol to about 70,000 g/mol;
   (b) a second vinylpyrrolidone/vinyl acetate copolymer having a molecular weight in the range of from about 30,000 g/mol to about 70,000 g/mol; and
   (c) a cosmetically acceptable carrier;
   wherein the first vinylpyrrolidone/vinyl acetate copolymer is not the same as the second vinylpyrrolidone/vinyl acetate copolymer wherein the combined amount of the first vinylpyrrolidone/vinyl acetate copolymer and the second vinylpyrrolidone/vinyl acetate copolymer is 2%; and
   wherein the weight ratio of the copolymer content of (a) to (b) is about 1:3, or is about 3:1.

2. The personal care composition of claim 1, wherein the second vinylpyrrolidone/vinyl acetate copolymer is dissolved in a solvent selected from the group consisting of alcohols, esters, ketones, and mixtures thereof.

3. The personal care composition of claim 1, wherein the composition further comprises water, a humectant, a preservative, an exfoliator, a lubricant, an emollient, and an emulsifier.

4. The personal care composition of claim 1, wherein the composition is selected from a lotion; a cream; an ointment; a balm; a salve; and a topical gel.

5. The personal care composition of claim 1, wherein a 20-micrometer layer of the composition, applied on the skin, reduces the transmission of ozone by at least 20% compared to a composition without the first vinylpyrrolidone/vinyl acetate copolymer and the second vinylpyrrolidone/vinyl acetate copolymer.

6. The personal care composition of claim 1, wherein (a) and (b) are mixed sequentially in the cosmetically acceptable carrier.

* * * * *